(12) United States Patent
Jackson et al.

(10) Patent No.: US 7,935,841 B2
(45) Date of Patent: May 3, 2011

(54) BISPHOSPHOLANES FOR USE AS CATALYSTS IN ASYMMETRIC REACTIONS

(75) Inventors: Philip M. Jackson, Cambridge (GB); Ian Campbell Lennon, Cambridge (CA); Martin E. Fox, Royston (GB)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 12/297,938

(22) PCT Filed: Apr. 18, 2007

(86) PCT No.: PCT/US2007/009500
§ 371 (c)(1),
(2), (4) Date: Oct. 30, 2008

(87) PCT Pub. No.: WO2007/123957
PCT Pub. Date: Nov. 1, 2007

(65) Prior Publication Data
US 2009/0099358 A1      Apr. 16, 2009

Related U.S. Application Data

(60) Provisional application No. 60/794,063, filed on Apr. 21, 2006.

(51) Int. Cl.
*C07F 9/30* (2006.01)
*C07F 17/02* (2006.01)
(52) U.S. Cl. .......................................... 556/20; 556/143
(58) Field of Classification Search .................... 556/20, 556/143
See application file for complete search history.

(56) References Cited

FOREIGN PATENT DOCUMENTS
WO        02/02500 A1    1/2002

OTHER PUBLICATIONS

Axtell, et al. Organometallics, 28(10), 2009, 2993-2999.*
W. Tang, et al., "New Chiral Phosphorus Ligands for Enantioselective Hydrogenation", Chemical Reviews, vol. 103, pp. 3029-3069, 2003.
I. C. Lennon, et al., "Asymmetric Hydrogenation of Pharmaceutically Interesting Substrates", Current Opinion in Drug Discovery & Development, vol. 6, pp. 855-875, 2003.
I. C. Lennon, et al., "The Application of Asymmetric Hydrogenation for the Manufacture of Pharmaceutical Intermediates: The Need for Catalyst Diversity", Synthesis, vol. 11, pp. 1639-1642, 2003.
M. J. Burk, "Modular Phospholane Ligands in Asymmetric Catalysis", Accounts of Chemical Research, vol. 33, pp. 363-372, 2000.
M. J. Burk, et al., "Preparation and Use of C2-Symmetric Bis(phospholanes): Production of a-Amino Acid Derivatives via Highly Enantioselective Hydrogenation Reactions", Journal American Chemical Society, vol. 115, pp. 10125-10138, 1993.
M. J. Burk, et al., "New Chiral 1,1'-Bis(Phospholano)ferrocene Ligands for Asymmetric Catalysis", Tetrahedron Letters, vol. 35, pp. 9363-9366, 1994.
J. Holz, et al., "Synthesis of a New Chiral Bisphospholane Ligand for the Rh(I)-Catalyzed Enantioselective Hydrogenation of Isomeric B-Acylamido Acrylates", Journal of Organic Chemistry, vol. 68, pp. 1701-1707, 2003.
W. Li, et al., "Synthesis of Chiral Hydroxyl Phospholanes from D-Mannitol and Their Use in Asymmetic Catalytic Reactions", Journal of Organic Chemistry, vol. 65, pp. 3489-3496, 2000.
J. Holz, et al., Synthesis of a New Class of Functionalized Chiral Bisphospholane Ligands and the Application in Enantioselective Hydrogenations, Journal of Organic Chemistry, vol. 63, pp. 8031-8034, 1998.
Q. Dai, et al, "Chiral Bisphospholane Ligands (Me-ketalphos): Synthesis of Their Rh(I) Complexes and Applications in Asymmetric Hydrogenation", Tetrahedron, vol. 62, pp. 868-871, 2006.
G. Hoge, "Stereoselective Cyclization and Pyramidal Inversion Strategies for P-Chirogenic Phospholane Synthesis", Journal of American Chemical Society, vol. 126, pp. 9920-9921, 2004.
C. J. Pilkington, et al., "Expanding the Family of Phospholane-Based Ligands: 1,2(Bis(2,5-diphenylphospholano) Ethane", Organic Letters, vol. 5, pp. 1273-1275, 2003.
F. Guillen, et al. "Synthesis and First Applications of a New Family of Chiral Monophosphine Ligand: 2,5-Diphenylphosphospholanes", Tetrahedron, vol. 58, pp. 5895-5904, 2002.
J. J. Bishop, et al., "Symmetrically Disubstituted Ferrocenes I. The Synthesis of Potential Bidentate Ligands", Journal of Organometatlic Chemistry, vol. 27, pp. 241-249, 1971.

(Continued)

*Primary Examiner* — James O Wilson
*Assistant Examiner* — Douglas M Willis
(74) *Attorney, Agent, or Firm* — Thomas C. McKenzie; Robert A. Franks; Balaram Gupta

(57) ABSTRACT

The invention concerns an enantiomerically enriched compound of formula (1) or the opposite enantiomer thereof

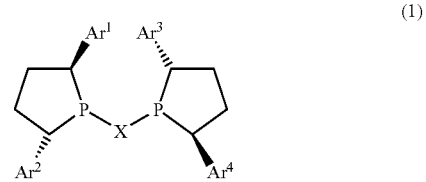

(1)

wherein each of $Ar^1$—$Ar^4$ represent the same or different aromatic groups of up to 20 carbon atoms and the bridging group X is the formula (5) in

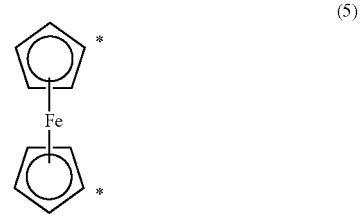

(5)

which * denotes points of attachment to phosphorus atoms and methods of making thereof.

5 Claims, No Drawings

OTHER PUBLICATIONS

E. Tyrell, et al., "The Application of H Nuclear Magnetic Resonance Spectroscopy for the Determination of the Absolute Configuration of Chiral Carboxylic Acids", Tetrahedron, vol. 52, pp. 9841-9852, 1996.

M. B. Watson, et al., "The Absolute Configurations of Some Aryl-and Alkyl-Substituted 3-Phenylpropanoic Acids", Journal of Chemical Society, vol. (C), pp. 258-262, 1968.

R. Goeschke, et al., "The Nonchiral Bislactim Diethoxy Ether as a Highly Stereo-Inducing Synthon for Sterically Hindered, y-Branced a-Amino Acids: A Practical, Large-Scale Route to an Intermediate of the Novel Renin Inhibitor Aliskiren", Helvetica Chimica Acta, vol. 86, pp. 2848-2871, 2003.

T. Sturm, et al., "A Novel Class of Ferrocenyl—Aryl-Based Diphosphine Ligands for Rh-and Ru-Catalyzed Enantioselective Hydrogenation", Advanced Synthesis Catalysis, vol. 345, pp. 160-164, 2003.

* cited by examiner

BISPHOSPHOLANES FOR USE AS CATALYSTS IN ASYMMETRIC REACTIONS

FIELD OF THE INVENTION

This invention relates to improved phosphine ligands and catalysts derived therefrom that are useful for asymmetric hydrogenation processes and for other asymmetric reactions.

BACKGROUND TO THE INVENTION

Homogeneous catalytic asymmetric hydrogenation is an important reaction for providing chiral intermediates for pharmaceutical agents and other products useful in the life sciences, required in the necessary single stereoisomeric form. In the ongoing quest to design more selective and more efficacious pharmaceutical agents, added structural complexity means that when an asymmetric hydrogenation approach to such agents is contemplated, the existing catalysts may not provide manufacturing solutions in every case and hence design of novel catalysts continues to be an important endeavour.

The majority of known catalysts for asymmetric hydrogenation take the form of transition metal complexes of chiral phosphorus-containing ligands, which are either monodentate or more commonly bidentate. Diphosphines represent the most widely investigated and industrially significant class of such bidentate ligands and a very large number of these ligands are reported in the literature [W. Tang and X. Zhang, *Chem. Rev.* 2003, 103, 3029-3069; I. C. Lennon and P. H. Moran, *Curr. Opin. Drug Discovery Dev.* 2003, 6, 855-875]. Bisphospholanes represent a subclass of diphosphines that has proved especially useful in pharmaceutical applications [I. C. Lennon and C. J. Pilkington, *Synthesis*, 2003, 1639-1642; M. J. Burk, *Acc. Chem. Res.* 2000, 33, 363-372]. Since the introduction of the pioneering DuPhos family of bisphospholanes, as represented by general formula (A),

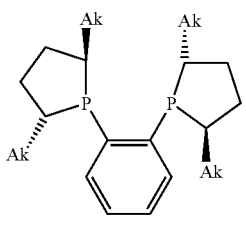

(A)

Ak = Me, Et, n-Pr, i-Pr numerous alternative bisphospholanes have been reported, based on the following structural variations:

(a) Different backbone structures to 1,2-diphenylene linking the phosphine groups. Ligands of formulae (B) to (D) are representative examples [M. J. Burk, J. E. Feaster, W. A. Nugent and R. L. Harlow, *J. Am. Chem. Soc.* 1993, 115, 10125-10138; M. J. Burk and M. F. Gross, *Tetrahedron Letters*, 1994, 35, 9363-9366; J. Holz, A. Monsees, H. Jiao, J. You, I. V. Komarov, C. Fischer, K. Drauz and A. Borner, *J. Org. Chem.* 2003, 68, 1701-1707].

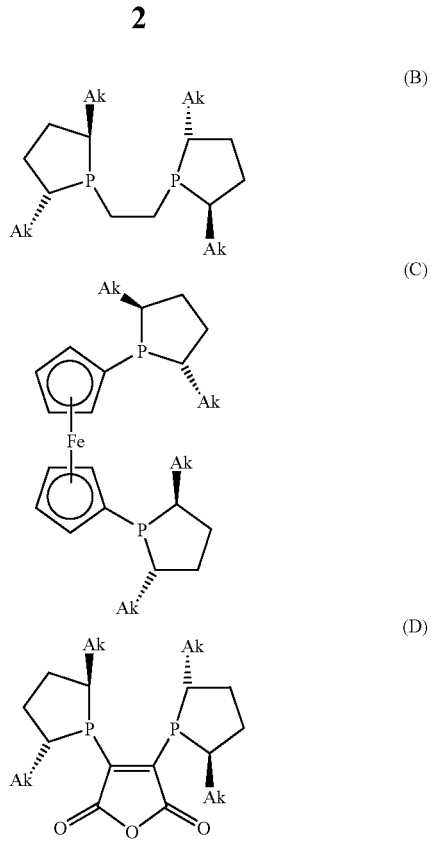

(b) Introduction of extra substituents at the 3-position and/or 4-position of each phospholane ring. The ligand of formula (E) is a representative example [W. Li, Z. Zhang, D. Xiao, X. Zhang *J. Org. Chem.* 2000, 65, 3489-3496; J. Holz, M. Quirmbach, U. Schmidt, D. Heller, R. Stümer and A. Borner, *J. Org. Chem.* 1998, 63, 8031-8034; Q. Dai; C-J. Wang, X. Zhang, *Tetrahedron* 2006, 62, 868-871].

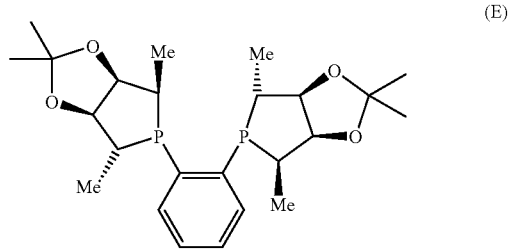

(c) The 2-position of each phospholane ring has an alkyl substituent but the 5-position is unsubstituted. This renders such ligands chiral by virtue of the phosphorus atom becoming a chiral centre and accordingly such ligands have been described as "P-chirogenic". The ligand of formula (F) is a representative example [G. Hoge, *J. Am. Chem. Soc.* 2004, 126, 9920-9921].

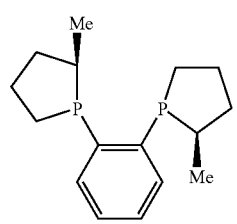

(d) The alkyl substituents at the 2- and 5-positions of each pholane rings are replaced by aryl substituents. To date, the only ligand reported with this structural variation and characterised for catalysis of asymmetric hydrogenation is Ph-BPE (G) (C. J. Pilkington and A. Zanotti-Gerosa, *Org. Lett.* 2003, 5, 1273-1275).

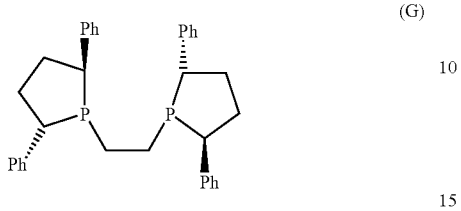
(G)

General synthetic methods first introduced for the DuPhos family of ligands and applicable to make ligands of types (a)-(c) are not applicable to ligands of type (d) so access to the latter presents technical challenges. For the first time, the present invention serves to significantly broaden the structural diversity of ligands of type (d), leading to enhanced diversity in the catalyst performance (as characterised by substrate scope, enantioselectivity and activity) of the corresponding transition metal complexes.

SUMMARY OF THE INVENTION

The present invention is based around the design and discovery of novel bisphospholane ligands having utility as components of catalysts for selective and efficient asymmetric hydrogenation processes and for other asymmetric reactions. One aspect of this invention relates to an enantiomerically enriched compound of formula (1) or the opposite enantiomer thereof

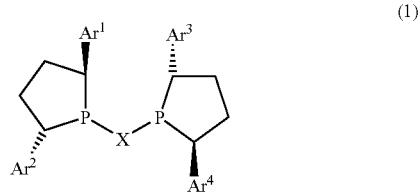
(1)

wherein each of $Ar^1$—$Ar^4$ represent the same or different aromatic groups of up to 20 carbon atoms and the bridging group X is selected from the group consisting of $CH_2$ and structural fragments according to formulae (2) to (5) in which * denotes points of attachment to phosphorus atoms, Y in (2) is O or N-alkyl and R in (4) is H or alkyl.

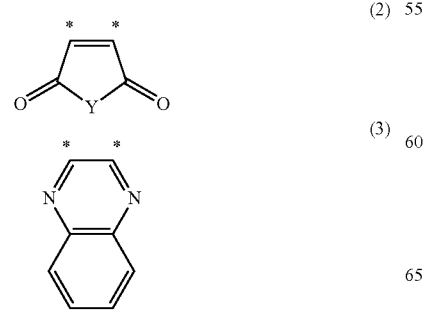
(2)

(3)

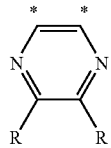
(4)

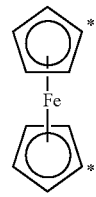
(5)

The invention further relates to metal-ligand complex catalysts comprising a transition metal complexed with a compound of formula (1) and application of these catalysts in asymmetric hydrogenation processes and for other asymmetric reactions. The invention yet further relates to novel intermediates required in the preparation of a compound of formula (1) containing, as bridging group, $CH_2$ or the structural fragment of formula (5).

DETAILED DESCRIPTION OF THE INVENTION

In the novel bisphospholanes (1) of the present invention, preferably each of $Ar^1$—$Ar^4$ is the same, more preferably each of $Ar^1$—$Ar^4$ is phenyl or substituted phenyl and most preferably each of $Ar^1$—$Ar^4$ is phenyl. A specific embodiment of the latter sub-class of ligands consists of compounds of formulae (6) to (10), either as the (R,R)-enantiomers depicted or as the opposite (S,S)-enantiomers.

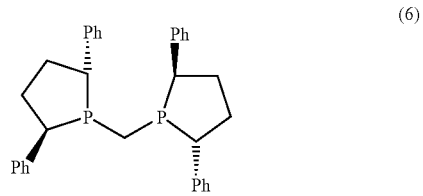
(6)

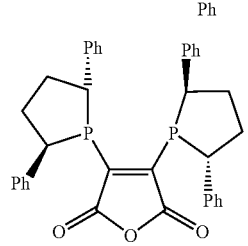
(7)

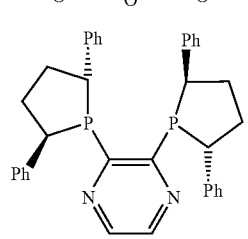
(8)

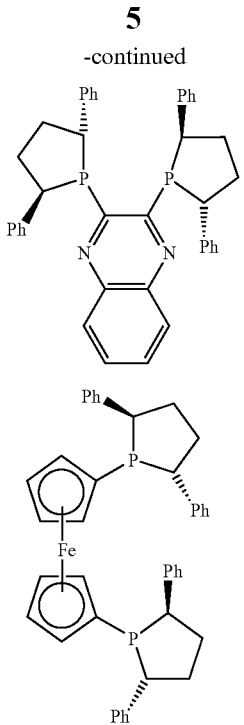

Synthetic routes to compounds of formulae (6) to (10), as described in the examples below, proceed by way of reactants containing a pre-formed trans-2,5-diphenylphospholane unit that is suitably activated for coupling reactions. This represents another aspect of the invention. In the case of the compound of formula (6), the synthetic method comprises the following steps for the (R,R)-enantiomer or equivalent steps for the (S,S)-enantiomer, and proceeds by way of novel reactants (12) and (13):

(a) conversion of the (R,R)-2,5-trans-diphenylphospholane-borane adduct (11) to (R,R)-(2,5-diphenylphospholan-1-yl) methanol borane adduct (12) preferably by treatment with formaldehyde or a formaldehyde equivalent, preferably paraformaldehyde, in the presence of a base. Preferred bases may be selected from alkali metal hydroxides, alkali metal alkoxides and organolithium compounds. More preferred bases are potassium hydroxide and sodium hydroxide, with potassium hydroxide being most preferred. Reaction solvents are selected to be compatible with the particular base used, for example organolithium compounds typically require an ethereal solvent, preferably tetrahydrofuran. Alkali metal hydroxides require a protic solvent selected from $C_{1-4}$ alcohols, water and mixtures thereof, optionally in the presence of a miscible ethereal cosolvent selected from tetrahydrofuran, 1,4-dioxane, 1,2-dimethoxyethane and bis(2-methoxyethyl) ether. Preferably, the protic solvent is a $C_{1-4}$ alcohol and more preferably it is methanol. The operating temperature is in the range of −78 to +40° C., preferably in the range of −10 to +30° C., and more preferably in the range of 20 to 30° C.

(b) conversion of (R,R)-(2,5-diphenylphospholan-1-yl) methanol borane adduct (12) to an activated O-sulfonyl derivative (13) wherein $R^1$ is alkyl, fluoroalkyl or aryl and preferably is trifluoromethyl, preferably by treatment with the corresponding sulfonic acid anhydride or sulfonic acid chloride. For the preferred embodiment of $R^1$ is trifluoromethyl, triflic anhydride is the preferred reagent. The base is preferably an amine, pyridine or a substituted pyridine, more preferably triethylamine or diisopropylethylamine and most preferably triethylamine. The reaction solvent is an aprotic solvent, preferably dichloromethane, toluene, diethyl ether, tert-butyl methyl ether, tetrahydrofuran, 1,4-dioxane, 1,2-dimethoxyethane and bis(2-methoxyethyl)ether, or mixtures thereof. More preferably, the reaction solvent is dichloromethane. The operating temperature is in the range of −78 to +30° C., or, for the preferred embodiment of $R^1$ is trifluoromethyl, in the range of range of −78 to 0° C., preferably −30 to 0° C.

(c) coupling of the O-sulfonyl derivative (13) with (R,R)-2,5-trans-diphenylphospholane-borane adduct (11) in the presence of an organolithium base to give the borane adduct of (R,R)-(6). The organolithium base may be selected from $C_{1-6}$ alkyl lithium compounds, phenyl lithium, lithium diisopropylamide and lithium hexamethyldisilazide. Preferably, the organolithium base is n-butyl lithium, sec-butyl lithium, tert-butyl lithium, methyl lithium or n-hexyl lithium and more preferably it is n-butyl lithium. The reaction solvent is an preferably an ethereal solvent selected from diethyl ether, tert-butyl methyl ether, tetrahydrofuran, 1,4-dioxane, 1,2-dimethoxyethane and bis(2-methoxyethyl)ether, and mixtures thereof. More preferably, the reaction solvent is tetrahydrofuran. A hydrocarbon solvent such as hexane may also present, typically as solvent for an alkyl lithium base added to the reaction mixture. The operating temperature will vary, dependent on the scale of operation, and is preferably in the range of −78 to 0° C. during the addition of reagents.

(d) removal of the borane component to give (R,R)-(6) as free ligand, preferably by treatment with an amine or diamine reagent. More preferably, the reagent is selected from 1,4-diazabicyclo[2.2.2]octane (DABCO), 1,5-diazabicyclo[4.3.0]non-5-ene, 1,8-diazabicyclo[4.4.0]undec-7-ene, N,N,N,N-tetramethylethylenediamine (TMEDA), morpholine, pyrrolidine and diethylamine. Most preferably, the reagent is DABCO. Toluene and tetrahydrofuran are preferred solvents and toluene is more preferred. The operating temperature is in the range of 10 to 110° C., preferably in the range of −10 to +30° C., and more preferably in the range of 20 to 30° C.

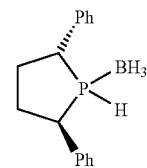

In the case of the compound of formula (10), the synthetic method comprises the following steps for the (R,R)-enantiomer or equivalent steps for the (S,S)-enantiomer, and proceeds by way of novel reactant (15):

(a) conversion of (R,R)-1-oxo-2,5-diphenylphospholane (14) to (R,R)-1-halogeno-2,5-diphenylphospholane (15), wherein halogeno (Z) is chloro or bromo. PZ₃ is the preferred reagent for this transformation. Preferred solvents may be selected from aromatic hydrocarbons, chlorinated aromatic hydrocarbons or ethers. From these general solvent classes, more preferred solvents are benzene, toluene, xylene, cumene, mesitylene, ethyl benzene, chlorobenzene, 1,2-dichlorobenzene, tetrahydrofuran, 1,4-dioxane, 1,2-dimethoxyethane and bis(2-methoxyethyl)ether. Toluene is the most preferred solvent. The operating temperature is in the range of −78 to +50° C., preferably in the range of −20 to +40° C., and more preferably in the range of 15 to 25° C.

(b) coupling of (R,R)-1-chloro-2,5-diphenylphospholane (15) with 1,1'-dilithioferrocene, preferably as its N,N,N,N-tetramethylethylenediamine (TMEDA) complex. Preferred solvents may be selected from aromatic hydrocarbons or ethers. From these general solvent classes, more preferred solvents are benzene, toluene, xylene, cumene, mesitylene, ethyl benzene, diethyl ether, tert-butyl methyl ether, tetrahydrofuran, 1,4-dioxane, 1,2-dimethoxyethane and bis(2-methoxyethyl)ether. Toluene is the most preferred solvent. The operating temperature is in the range of −78 to +30° C., preferably in the range of −20 to +30° C., and more preferably in the range of 10 to 25° C.

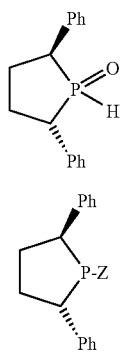

Another aspect of the present invention concerns novel transition metal complexes based on ligands according to formula (1) and utility of these complexes as catalysts for asymmetric hydrogenation processes and for other asymmetric reactions, including but not limited to hydroformylation, hydrocyanation, hydroesterification and hydrocarboxylation. In aforementioned transition metal complexes, preferred transition metals are rhodium, ruthenium, iridium, nickel and palladium. In application of such transition metal complexes to the catalysis asymmetric hydrogenation processes, the substrate undergoing stereoselective hydrogenation is preferably an olefin, a ketone or an imine. In such processes the transition metal is preferably rhodium, ruthenium or iridium and more preferably the transition metal is either rhodium or ruthenium. Thus, another preferred embodiment of this invention comprises providing a substrate selected from an olefin, a ketone or an imine and a catalyst complex comprising the ligands of formula 1 and a transition metal in a solvent for the substrate and the complex in the presence of hydrogen gas. Preferably, this reaction would occur at pressures above ambient pressure. The preferred temperature for the reaction is from 0 to 100° C., more preferably ambient to 70° C. The mole ratio of substrate to catalyst complex is preferably greater than 200:1, more preferably greater than 500:1, most preferably at least 1000:1. The maximum mole ratio will be limited by effectiveness of the reaction and is desired to be as high as possible but is generally not more than 100,000:1.

The invention is further illustrated by the following examples.

Example 1

Synthesis of 1,2-bis[(R,R)-2,5-diphenylphospholano]methane (i) (R,R)-2,5-trans-diphenylphospholane-borane adduct

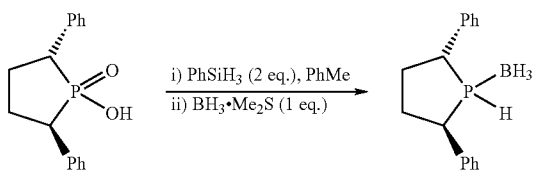

(R,R)-1-Hydroxy-1-oxo-2,5-trans-diphenylphospholane (40.1 g, 147.3 mmol; prepared according the method of Guillen, F et al. *Tetrahedron* 2002, 58, 5895) was suspended in toluene (450 ml). The mixture was degassed by evacuation and filling with nitrogen (×5) and then heated in an oil bath at 120° C. (internal temperature 100° C.). Phenylsilane (36.3 ml, 294.5 mmol) was added in portions over 2 h. The solution was heated for a further 2 h and then cooled to 5° C. Borane dimethyl sulfide complex (94%, 15 ml, 147.3 mmol) was added over 5 minutes. The mixture was allowed to warm to room temperature and stirred overnight. The solution was filtered through a pad of silica (100 g), eluting with toluene (600 ml). Concentrated under reduced pressure and crystallized from toluene/heptane (1:4, 150 ml). The solid was filtered and washed with toluene/heptane (1:4, 50 ml). Dried under vacuum to give the title compound (31.22 g, 83%).

¹H NMR (400 MHz, CDCl₃) δ ppm 7.2-7.4 (10H, m), 4.82 (1H, dq, $J_{HP}$ 361 Hz, $J_{HH}$ 11 Hz), 3.95 (1H, m), 3.52 (1H, m), 2.55-2.65 (2H, m), 2.15-2.25 (2H, m) and 0.1-0.9 (3H, br q, BH₃).

¹³C NMR (100 MHz, CDCl₃) δ ppm 138.1 (d, J 5 Hz), 136.9, 129.4, 129.1, 129.0, 128.9, 128.2, 127.7, 44.9 (d, J 33 Hz), 41.0 (d, J 29 Hz), 35.0 (d, J 4 Hz) and 34.3.

³¹P NMR (162 MHz, CDCl₃) δ ppm 30.1.

(ii) (R,R)-(2,5-Diphenylphospholan-1-yl)methanol borane adduct

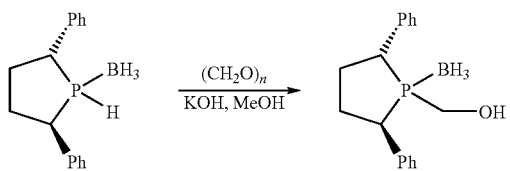

(R,R)-2,5-trans-diphenylphospholane-borane adduct (9.24 g, 36.4 mmol) and paraformaldehyde (9.2 g) were suspended in methanol (40 ml) at 20° C. under nitrogen. A solution of potassium hydroxide (4.64 g, 72.7 mmol) in methanol (50 ml) was added over 10 minutes (a clear solution soon forms). The mixture was stirred overnight and then acidified with 1M aqueous hydrochloric acid (80 ml). The product was extracted with ethyl acetate (2×100 ml) and washed with saturated sodium hydrogen carbonate solution (50 ml) and brine (50 ml). The organic phase was dried (MgSO₄), filtered and concentrated under reduced pressure. Heptane (30 ml) was added and the solid was filtered. Washed with ethyl acetate/heptane (1:4, 3×20 ml). Dried under vacuum to give the title compound (8.89 g, 86%).

$^1$H NMR (400 MHz, CDCl₃) δ ppm 7.45-7.25 (1H, m), 3.93-3.84 (1H, m), 3.73-3.65 (1H, m), 3.68 (2H, s), 2.65-2.17 (4H, m), 1.45 (1H, br) and 0.75 to −0.1 (3H, br q, BH₃).

$^{13}$C NMR (100 MHz, CDCl₃) δ ppm 137.2, 136.0 (d, J 5 Hz), 129.5, 129.0 (d, J 5 Hz), 128.9, 127.8 (d, J 2 Hz), 127.7 (d, J 3.5 Hz), 127.5 (d, J 3 Hz), 57.6 (d, J 30 Hz), 44.8 (d, J 30 Hz), 40.9 (d, J 28 Hz), 33.2 (d, J 5 Hz) and 31.0.

$^{31}$P NMR (162 MHz, CDCl₃) δ ppm 47.1 (br).

(iii) Trifluoromethanesulfonic acid (R,R)-2,5-diphenyl-phospholan-1-ylmethyl ester borane adduct

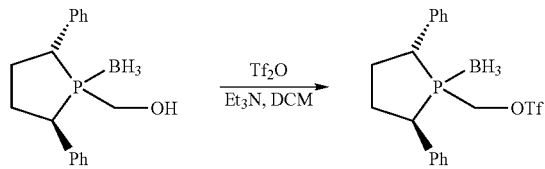

(R,R)-(2,5-Diphenylphospholan-1-yl)methanol borane adduct (4.70 g, 16.5 mmol) was dissolved in DCM (40 ml) under nitrogen and cooled to −30° C. Triethylamine (2.5 ml, 18.2 mmol) was added followed by triflic anhydride (3.10 ml, 18.2 mmol) dropwise over 5 minutes (temperature −30 to −27° C.). The reaction was stirred for 45 minutes and then quenched with water (20 ml). The organic phase was separated and washed with water (2×20 ml). Dried (MgSO₄) and filtered through a pad of silica eluting with DCM (50 ml). Evaporated under reduced pressure to give the title compound as a colourless oil (6.23 g, 90%).

$^1$H NMR (400 MHz, CDCl₃) δ ppm 7.40-7.25 (10H, m), 4.53 (1H, d, J 12 Hz), 4.20 (1H, dd, J 13, 3, Hz), 3.88-3.74 (2H, m), 2.76-2.48 (2H, m), 2.44-2.20 (2H, m) and 0.8 to −0.2 (3H, br q, BH₃).

$^{13}$C NMR (100 MHz, CDCl₃) δ ppm 135.4, 133.9 (d, J 6 Hz), 129.6, 129.2, 128.9 (d, J 5 Hz), 128.3, 128.1, 127.8 (d, J 4 Hz), 122.0 (d, J 320 Hz), 67.7 (d, J=16 Hz), 45.2 (d, J 30 Hz), 41.1 (d, J 26 Hz), 33.3 (d, J 6 Hz) and 30.8.

$^{31}$P NMR (162 MHz, CDCl₃) δ ppm 49.7.

(iv) 1,2-Bis[(R,R)-2,5-diphenylphospholano]methane-borane adduct

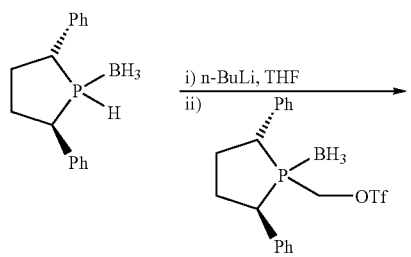

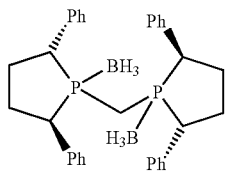

(R,R)-2,5-trans-diphenylphospholane-borane adduct (3.44 g, 13.54 mmol) was dissolved in dry THF (30 ml) under nitrogen. The solution was cooled to −65° C. Added a solution of n-BuLi (2.5 M in hexanes, 0.34 ml, 0.86 mmol) dropwise (temperature −60 to −65° C., initially there is insoluble substrate which dissolves as the BuLi is added to give a yellow solution). Stirred for 1 h and then added a solution of trifluoromethanesulfonic acid (R,R)-2,5-diphenyl-phospholan-1-ylmethyl ester borane adduct (6.20 g, 14.90 mmol) in dry THF (15 ml). Allowed to warm to room temperature and stirred overnight. Quenched with 1M aqueous HCl (30 ml). Separated the THF phase and concentrated under reduced pressure. The aqueous phase was extracted with DCM (2×30 ml). The DCM extracts were combined with the THF concentrate and washed with water (20 ml), dried (MgSO₄), and filtered through silica (25 g) eluting with DCM (50 ml). The solution was concentrated under reduced pressure and the residue crystallised from ethyl acetate/heptane (1:3, 16 ml). Filtered and washed with ethyl acetate/heptane (1:2, 2×6 ml) followed by ethyl acetate/heptane (1:1, 2 ml) Dried under vacuum to give the title compound (4.33 g, 610%).

$^1$H NMR (400 MHz, CDCl₃) δ ppm 7.35-7.0 (2H, m), 4.0-3.90 (2H, m), 2.58-2.42 (2H, m), 2.34-2.22 (2H, m), 2.0-1.86 (4H, m), 0.94 (2H, t, J 14 Hz) and 1.1-0.3 (6H, br).

$^{13}$C NMR (100 MHz, CDCl₃) δ ppm 138.2, 134.8 (d, J 5 Hz), 129.8 (d, J 5 Hz), 129.3, 128.5, 128.0, 127.7, 127.1, 49.1 (dd, J 30, 5 Hz), 43.1 (d, J 26 Hz), 36.3, 29.6 and 19.1 (t, J 16 Hz).

$^{31}$P NMR (162 MHz, CDCl₃) 3 ppm 43.9.

(v) 1,2-Bis[(R,R)-2,5-diphenylphospholano]methane

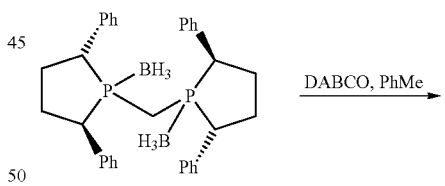

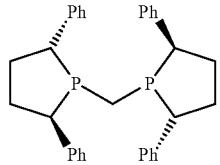

(R,R)-BPM (All Solvents were Degassed Prior to Use)

1,2-Bis[(R,R)-2,5-diphenylphospholano]methane-borane adduct (986 mg, 1.90 mmol) and DABCO (639 mg, 5.69 mmol) were charged to a 50 ml Schlenk flask. Deoxygenated by evacuation and filling with nitrogen (×5). Added toluene (10 ml). Heated in an oil bath at 60° C. (external temperature) for 2 h. Allowed to cool to room temperature with stirring overnight. Filtered through a pad of silica (6 g) under nitrogen, eluting with toluene (20 ml). Evaporated under reduced pressure to give a cloudy oil. Solidified by trituration with isopropanol (3 ml) and evaporated under reduced pressure to give the title compound (929 mg, 99%).

$^1$H NMR (400 MHz, CDCl$_3$) δ ppm 7.25-6.90 (20H, m), 3.60-3.50 (2H, m), 3.27-3.18 (2H, m), 2.36-2.24 (2H, m), 2.16-2.06 (2H, m), 1.94-1.70 (4H, m) and 0.68 (2H, m).

$^{13}$C NMR (100 MHz, CDCl$_3$) δ ppm 144.4 (t, J 8 Hz), 139.1, 128.7, 128.6, 128.3 (t, J 5 Hz), 128.1, 126.2, 125.8, 49.3 (t, J 5 Hz), 47.3 (t, J 5 Hz), 36.9, 31.8 and 22.0 (t, J 34 Hz).

$^{31}$P NMR (162 MHz, CDCl$_3$) δ ppm 4.5.

Example 2

Preparation of Transition Metal Catalyst Complexes of 1,2-bis[(R,R)-2,5-diphenylphospholano]methane (i) 1,2-Bis[(R,R)-2,5-diphenylphospholano]methane-(1,5-cyclooctadiene) rhodium(I) tetrafluoroborate

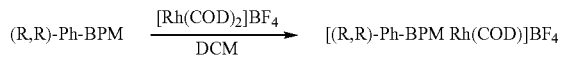

Bis[(R,R)-2,5-diphenylphospholano]methane (150 mg, 0.30 mmol) and bis(1,5-cyclooctadiene) rhodium(I) tetrafluoroborate (124 mg, 0.30 mmol) were added to a Schlenk flask. Evacuated and filled with nitrogen (×5). Added DCM (degassed; 3 ml) and stirred at room temperature overnight. The solution was evaporated under reduced pressure and the residue was triturated with ether (degassed; 2 ml) to give an orange solid. The supernatant liquid was removed by syringe and the solid was washed with ether (degassed; 3×2 ml) and pentane (degassed; 2×3 ml). Dried under vacuum to give the title compound (205 mg, 86%).

$^1$H NMR (400 MHz, CDCl$_3$) δ ppm 7.62-7.55 (8H, m), 7.47-7.40 (2H, m), 7.20-7.15 (6H, m), 6.81 (4H, d, J 8 Hz), 5.30 (2H, m), 3.70-3.60 (4H, m), 3.32-3.26 (2H, m), 3.15-2.98 (2H, m), 2.52-2.38 (6H, m), 2.25-2.15 (2H, m), 2.08-1.96 (4H, m), 1.70-1.60 (2H, m) and 1.38-1.28 (2H, m).

$^{13}$C NMR (100 MHz, CDCl$_3$) δ ppm 140.4, 135.3, 129.9, 129.4, 129.1, 128.3, 127.8, 127.4, 100.2, 99.7, 49.5, 47.3, 39.8 (t, J 20 Hz), 31.2, 30.6, 30.1 and 28.4.

$^{31}$P NMR (162 MHz, CDCl$_3$) δ ppm −6.9 (d, J 136 Hz). m/z (ESI) 703 (M-BF$_4$).

(ii) Chloro-{1,2-Bis[(R,R)-2,5-diphenylphospholano]methane}-cymene)ruthenium (II) chloride

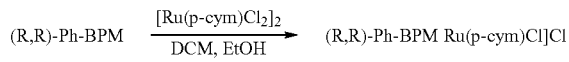

Bis[(R,R)-2,5-diphenylphospholano]methane (214 mg, 0.43 mmol) and dichloro(p-cymene) ruthenium (II) dimer (133 mg, 0.22 mmol) were added to a Schlenk flask. Evacuated and filled with nitrogen (×5). Added DCM (2 ml) and ethanol (4 ml) and heated in an oil bath at 70° C. for 2 h. The solution was evaporated under reduced pressure and the residue was triturated with pentane (5 ml). The mixture was filtered and dried under vacuum to give a yellow-brown solid (343 mg, 100%).

$^{31}$P NMR (162 MHz, CDCl$_3$) δ ppm 43.2 (d, J 83 Hz) and 29.9 (d, J 83 Hz). m/z (ESI) 763 (M-Cl, 100%), 593 (M-2Cl-cym, 93).

(iii) Dichloro-{1,2-Bis[(2R,5R)-2,5-diphenylphospholano]methane}[(1S,2S)-1,2-diphenylethylenediamine)]ruthenium (II)

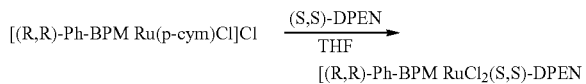

Chloro-{1,2-Bis[(2R,5R)-2,5-diphenylphospholano]methane} (p-cymene)ruthenium (II) chloride (320 mg, 0.40 mmol) and (1S,2S)-1,2-diphenylethylenediamine (85 mg, 0.40 mmol) were added to a Schlenk flask. Evacuated and filled with nitrogen (×5). Added THF (2 ml) and heated in an oil bath at 70° C. overnight. The solution was evaporated under reduced pressure to give a brown oil. Triturated with isopropanol (2 ml) and filtered. Washed with isopropanol (2×1 ml) and dried under vacuum to give the title compound as a yellow solid (265 mg, 75%).

$^1$H NMR (400 MHz, CDCl$_3$) δ ppm 7.53-7.47 (4H, m), 7.39 (4H, t, J 7 Hz), 7.31 (2H, t, J 7 Hz), 7.15-6.95 (16H, m), 6.85 (4H, m), 4.15-4.00 (4H, m), 3.45-3.35 (2H, m), 3.22 (2H, t, J 10 Hz), 2.85-2.73 (4H, m), 2.50-2.35 (2H, m), 2.28-2.10 (4H, m) and 1.95-1.80 (2H, m).

$^{13}$C NMR (100 MHz, CDCl$_3$) δ ppm 143.6, 141.9, 140.4, 130.1, 129.0, 128.5, 128.1, 127.7, 127.1, 126.0, 125.9, 64.4, 62.7, 48.2, 44.4, 34.8, 33.8 and 25.4.

$^{31}$P NMR (162 MHz, CDCl$_3$) δ ppm 50.2.

Example 3

Asymmetric Hydrogenation Processes Using Transition Metal Catalyst Complexes of 1,2-bis[(R,R)-2,5-diphenylphospholano]methane (i) Hydrogenation of Dimethyl Itaconate

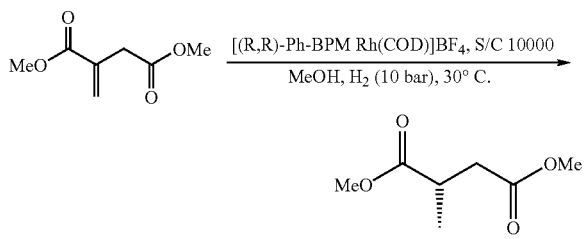

The reaction was carried out in an Argonaut Endeavor hydrogenation vessel. The glass liner was charged with dimethyl itaconate (1.58 g, 10.0 mmol) and 1,2-bis[(R,R)-2,5-diphenylphospholano]methane-(1,5-cyclooctadiene) rhodium(I) tetrafluoroborate (0.8 mg, 0.001 mmol, S/C 10000). Charged to 10 bar nitrogen and vented (×5). Added degassed methanol (4 ml). Charged to 10 bar nitrogen and vented (×2). Commenced stirring at 1000 rpm and heated to 30° C. Charged to 10 bar H$_2$ and monitored hydrogen uptake (reaction complete after 15 minutes). Cooled to room temperature, vented and evaporated to give (S)-2-methylsuccinic acid dimethyl ester, conversion 100%, ee 99.5% (Cbiraldex GTA, 15 m×0.25 mm, injector/detector 180° C., helium 14 psi, 90° C. for 6 min then ramp at 1° C./min to 105° C., retention times R 9.81 minutes, S 10.03 minutes).

(ii) Hydrogenation of methyl 2-acetamidoacrylate

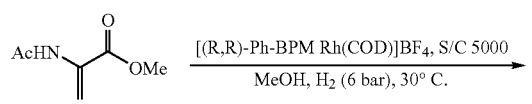

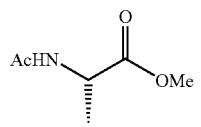

(S)-2-Acetylaminopropionic acid methyl ester, conversion>99%, ee>99% (Chirasil Dex CB, 25 m×0.25 mm, injector/detector 200° C., helium 20 psi, 130° C. for 10 minutes then ramp at 10° C./min to 200° C., retention times S 3.10 minutes, R 3.21 minutes).

(iii) Hydrogenation of 2-acetamidoacrylic acid

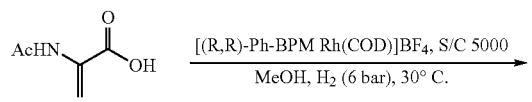

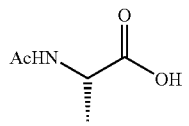

(S)-2-Acetylaminopropionic acid methyl ester, conversion>99%, ee>99% (derivatised using TMS-diazomethane and then analysed using the same method developed for the methyl ester).

(iv) Hydrogenation of Methyl acetamidocinnamate

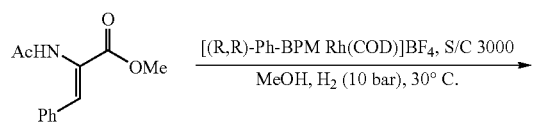

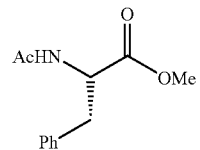

(S)-2-Acetylamino-3-phenyl-propionic acid methyl ester, conversion 100%, ee 99% (Chirasil Dex CB, 25 m×0.25 mm, injector/detector 200° C., helium 20 psi, 150° C. for 25 minutes then ramp at 10° C./min to 200° C., retention times R 19.10 minutes, S 19.64 minutes).

(v) Hydrogenation of 2-(tert-Butoxycarbonyl-methyl-amino)-3-(3,4-dichloro-phenyl)acrylic acid

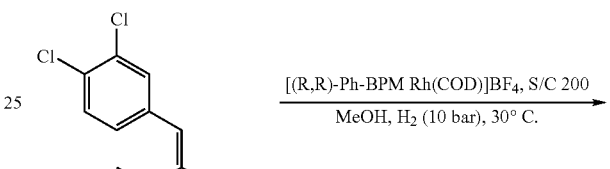

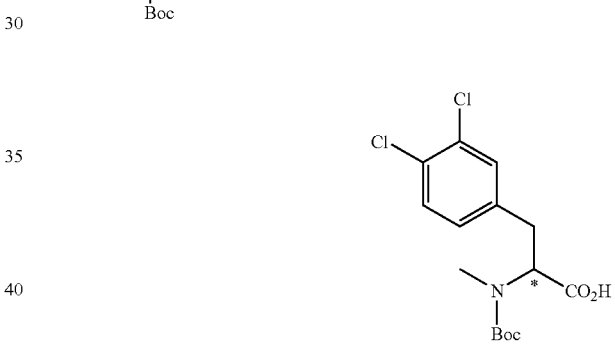

2-(tert-Butoxycarbonyl-methyl-amino)-3-(3,4-dichloro-phenyl)-propionic acid, conversion 96%, ee 95% (HPLC, Chirobiotic R, 250 mm×4.6 mm, MeOH/0.1% TEA acetate pH 4.75 (40:60), 0.5 ml/min, ambient temperature, detection UV 230 nm, retention times 16.79 minutes and 21.53 minutes).

(vi) Hydrogenation of 2-Cyclohexylmethylene-succinic Acid 1-methyl ester

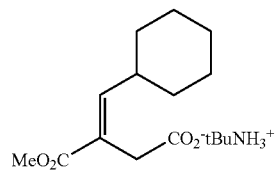

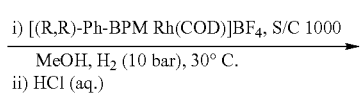

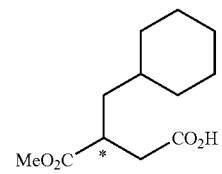

2-Cyclohexylmethyl-succinic acid 1-methyl ester, conversion 100%, ee 91% (Chirasil Dex CB, 25 m×0.25 mm, injector/detector 200° C., helium 20 psi, 50° C. for 2 minutes then ramp at 10° C./min to 200° C., hold for 5 minutes, retention times 16.00 minutes and 16.06 minutes).

(vii) Hydrogenation of N-(1-phenylethylidene)aniline

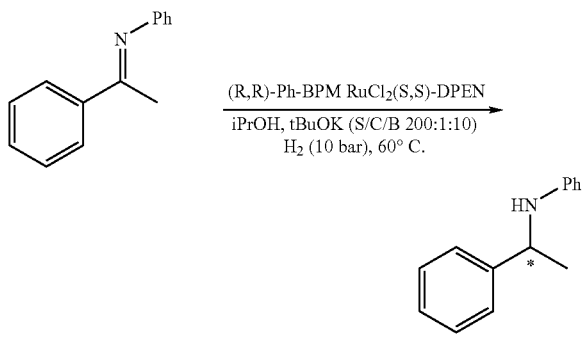

The reaction was carried out in a multiwell hydrogenation vessel. Dichloro-{1,2-Bis[(2R,5R)-2,5-diphenylphospholano]methane}[(1S,2S)-1,2-diphenylethylenediamine)] ruthenium (II) (2.2 mg, 0.0025 mmol) was suspended in degassed isopropanol (2 ml) in a Schlenk flask under nitrogen. Added potassium tert-butoxide (1M in tert-butanol, 0.025 ml) and heated until a yellow solution was obtained. The glass liner was charged with N-(1-phenylethylidene) aniline (98 mg, 0.50 mmol). Charged to 10 bar nitrogen and vented (×5). Added the precatalyst solution and charged to 10 bar nitrogen and vented (×2). Commenced stirring at 1000 rpm and heated to 60° C. Charged to 10 bar $H_2$ and stirred for 18 h. Cooled to room temperature, vented and evaporated to give phenyl-(1-phenylethyl)amine, conversion>99%, ee 71% (GC, sample derivatised by treatment with acetic anhydride pyridine, Chirasil DEX CB, 25 m×0.25 mm, injector/detector 200° C., helium 20 psi, 140° C. for 20 minutes then ramp at 5° C./min to 200° C., hold for 5 minutes, retention times 23.21 minutes and 23.45 minutes).

(viii) Hydrogenation of N-(1-phenylethylidene)benzylamine

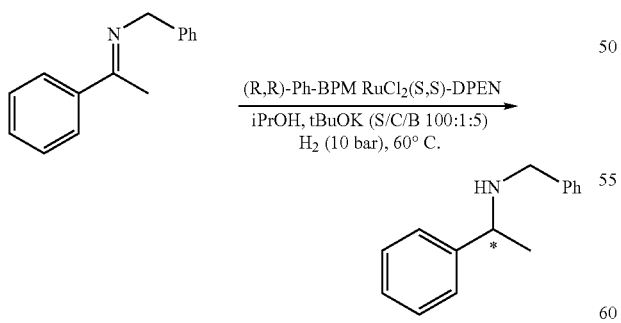

Benzyl-(1-phenylethyl)amine, conversion>99%, ee 82% (GC, sample derivatised by treatment with acetic anhydride pyridine, Chirasil DEX CB, 25 m×0.25 mm, injector/detector 200° C., helium 20 psi, 170° C. for 40 minutes then ramp at 15° C./min to 200° C., retention times 29.71 minutes and 30.73 minutes).

(iv) Hydrogenation of 1-methyl-6,7-dimethoxy-3,4-dihydroisoquinoline

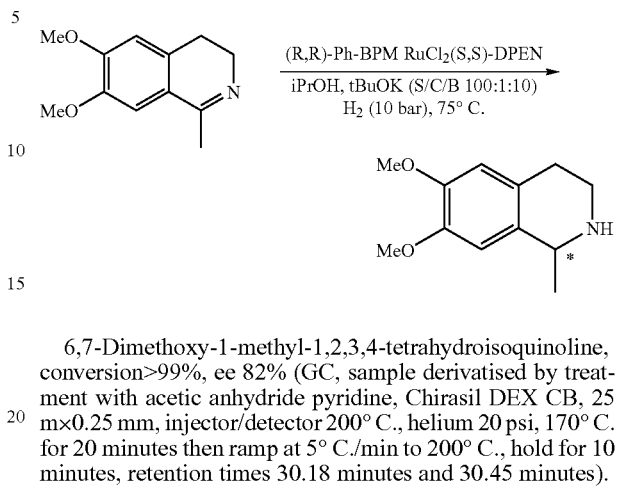

6,7-Dimethoxy-1-methyl-1,2,3,4-tetrahydroisoquinoline, conversion>99%, ee 82% (GC, sample derivatised by treatment with acetic anhydride pyridine, Chirasil DEX CB, 25 m×0.25 mm, injector/detector 200° C., helium 20 psi, 170° C. for 20 minutes then ramp at 5° C./min to 200° C., hold for 10 minutes, retention times 30.18 minutes and 30.45 minutes).

Example 4

Synthesis of 3,4-Bis[(S,S)-2,5-diphenyl-phospholan-1-yl]furan-2,5-dione

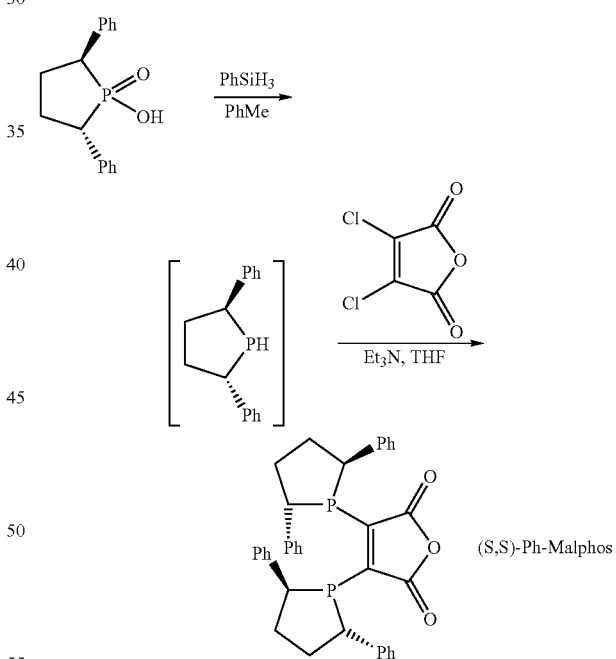

(S,S)-1-hydroxy-1-oxo-2,5-trans-diphenylphospholane (600 mg, 2.20 mmol) was suspended in toluene (6 ml). The mixture was degassed by evacuation and filling with nitrogen (×5) and then heated in an oil bath at 110° C. (external temperature). Phenylsilane (0.54 ml, 4.41 mmol) was added in one portion and the mixture was heated for 2 h (during this time vigorous effervescence is observed and a clear solution forms). The solution was cooled to room temperature and the solvent was evaporated under reduced pressure. The crude phosphine was further dried under high vacuum (2.9 mbar, 60° C.). The residue was cooled to room temperature and dissolved in THF (3 ml) under nitrogen. Triethylamine (0.31 ml, 2.20 mmol) was added, followed by a solution of 2,3-dichloromaleic anhydride (167 mg, 1.00 mmol) in THF (2 ml). The mixture was heated in an oil bath at 60° C. (external temperature) and stirred for 18 h (dark purple solution forms). The solution was cooled to room temperature and solvent was evaporated under reduced pressure. The residue was chromatographed on silica, eluting with DCM/heptane (2:3) to give a deep red oil which solidified on standing (180 mg, 0.31 mmol, 31%).

$^1$H NMR (400 MHz, CDCl$_3$) δ ppm 7.51-7.34 (10H, m), 6.90 (4H, d, J 8 Hz), 6.80 (2H, t, J 7 Hz), 6.56 (4H, t, J 8 Hz), 4.60-4.53 (2H, m), 4.05-3.93 (2H, m), 2.73-2.61 (2H, m), 2.58-2.45 (2H, m), 2.44-2.35 (2H, m) and 1.97-1.85 (2H, m).

$^{13}$C NMR (100 MHz, CDCl$_3$) δ ppm 161.7, 156.2 (m), 141.1 (t, J 11 Hz), 136.6, 127.1, 127.0, 126.9, 126.8, 125.0, 124.9, 124.7, 48.2 (d, J 7 Hz), 41.1 (d, J 5 Hz), 38.0 and 31.6.

$^{31}$P NMR (162 MHz, CDCl$_3$) δ ppm 3.5.

Example 5

Synthesis of 3,4-Bis[(S,S)-2,5-diphenyl-phospholan-1-yl]-furan-2,5-dione-(1,5-cyclooctadiene) rhodium (I) tetrafluoroborate

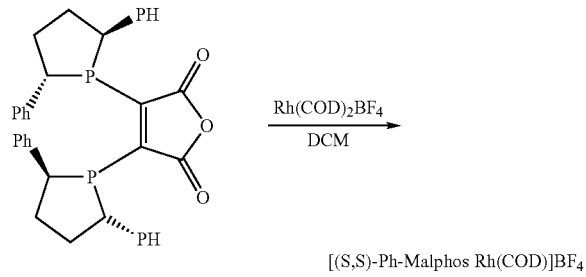

[(S,S)-Ph-Malphos Rh(COD)]BF$_4$ (S,S)-Ph-Malphos (102 mg, 0.178 mmol) and [Rh(COD)$_2$]BF$_4$ (72 mg, 0.178 mg) were charged to a 25 ml Schlenk flask. The flask was evacuated and filled with nitrogen (×5). Degassed DCM (2 ml) was added (a dark brown solution forms) and the mixture was stirred overnight. The solvent was evaporated and the residue was triturated with degassed ether (3 ml). The solid was filtered under nitrogen, washed with degassed ether (2×2 ml) and dried to give the title compound as a brown solid (133 mg, 0.15 mmol, 86%).

$^1$H NMR (400 MHz, CDCl$_3$) δ ppm 7.41-7.36 (4H, m), 7.30-7.26 (6H, m), 7.22-7.18 (6H, m), 7.11-7.07 (4H, m), 5.68-5.62 (2H, m), 4.51-4.36 (4H, m), 4.00 (2H, dd, J 13, 6 Hz), 3.08-2.94 (2H, m), 2.66-2.43 (6H, m), 2.05-1.96 (2H, m), 1.82-1.71 (2H, m), 1.31 1.13 (4H, m).

$^{31}$P NMR (162 MHz, CDCl$_3$) δ ppm 62.8 (d, J 154 Hz).

Example 6

Synthesis of (S,S)-2,3-Bis(2,5-diphenyl-phospholan-1-yl)-quinoxaline

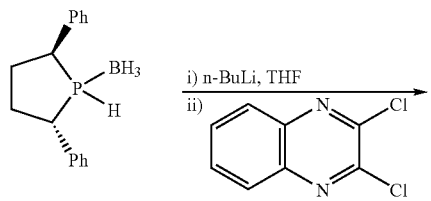

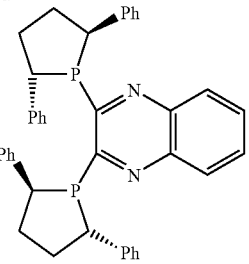

(S,S)-2,5-trans-Diphenylphospholane-borane adduct (381 mg, 1.50 mmol) was dissolved in dry THF (3 ml) under nitrogen. The solution was cooled to –20° C. A solution of n-BuLi (2.5 M in hexanes, 0.6 ml, 1.50 mmol) was added dropwise and the mixture was stirred for 30 minutes (a yellow solution is formed). 2,3-Dichloroquinoxaline (136 mg, 0.68 mmol) was added in one portion and the residues were washed in with dry THF (1 ml) (the quinoxaline is only sparingly soluble in THF). The mixture was allowed to warm to room temperature (red/orange solution is observed). The reaction mixture was stirred overnight and then quenched with 1M aqueous HCl (5 ml) (effervescence was observed) and extracted with ethyl acetate (10 ml). The organic solution was washed with water (5 ml) and brine (5 ml), dried (MgSO$_4$), filtered and concentrated under reduced pressure. The residue was chromatographed on silica, eluting with DCM/heptane (2:3) to give a yellow solid (200 mg, 0.33 mmol, 48%).

$^1$H NMR (400 MHz, CDCl$_3$) δ ppm 8.11-8.06 (2H, m), 7.77-7.73 (2H, m), 7.36-7.21 (10H, m), 6.37 (2H, t, J 8 Hz), 6.29 (4H, d, J 8 Hz), 6.07 (4H, t, J 8 Hz), 4.53-4.46 (2H, m), 3.83-3.73 (2H, m), 2.58-2.45 (2H, m), 2.09-1.99 (4H, m) and 1.87-1.75 (2H, m).

$^{13}$C NMR (100 MHz, CDCl$_3$) δ ppm 163.2 (br d), 144.2 (t, J 10 Hz), 141.2, 139.8, 129.4, 129.2, 129.1 (t, J 5 Hz), 128.1, 127.4, 126.9, 125.7, 125.4, 49.6 (t, J 10 Hz), 43.3, 37.9 and 33.7.

$^{31}$P NMR (162 MHz, CDCl$_3$) δ ppm 9.1.

Example 7

Synthesis of (S,S)-2,3-Bis(2,5-diphenyl-phospholan-1-yl)-(1,5-cyclooctadiene) rhodium(I) tetrafluoroborate

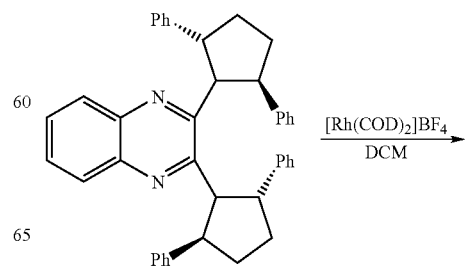

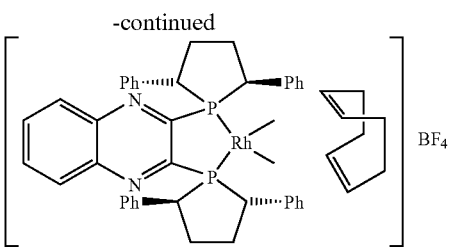

2,3-Bis[(S,S)-2,5-diphenyl-phospholan-1-yl]-quinoxaline (104 mg, 0.171 mmol) and [Rh(COD)$_2$]BF$_4$ (70 mg, 0.171 mg) were charged to a 25 ml Schlenk flask. The flask was evacuated and filled with nitrogen (×5). Degassed DCM (2 ml) was added (a deep red solution forms) and the mixture was stirred for 3 h. The solvent was evaporated and the residue was triturated with degassed ether (3 ml). The solid was filtered under nitrogen, washed with degassed ether (2×2 ml) and dried to give the title compound as an orange solid (119 mg, 0.13 mmol, 77%).

$^1$H NMR (400 MHz, CDCl$_3$) δ ppm 8.38 (2H, dd, J 6, 4 Hz), 8.15 (2H, dd, J 7, 4 Hz), 7.30-7.23 (6H, m), 7.02-6.93 (6H, m), 6.83-6.75 (8H, m), 5.75-5.69 (2H, m), 4.77-4.67 (2H, m), 4.33-4.26 (2H, m), 3.98-3.90 (2H, m), 3.09-2.97 (2H, m), 2.88-2.75 (2H, m), 2.61-2.47 (4H, m), 2.27-2.18 (2H, m), 1.93-1.81 (2H, m), 1.76-1.65 (2H, m) and 1.35-1.25 (2H, m).

$^{13}$C NMR (100 MHz, CDCl$_3$) δ ppm 156.4 (t, J 49 Hz), 142.6, 138.6, 135.3, 134.1, 130.4, 129.3, 128.8, 128.3, 127.8 (d, J 11 Hz), 105.1 (m), 98.9 (m), 53.0 (t, J 8 Hz), 49.8 (t, J 10 Hz), 33.8, 31.9, 31.8 and 28.2.

$^{31}$P NMR (162 MHz, CDCl$_3$) δ ppm 58.6 (d, J 151 Hz).

Example 8

Synthesis of (R,R)-2,3-Bis(2,5-diphenyl-phospholan-1-yl)-pyrazine

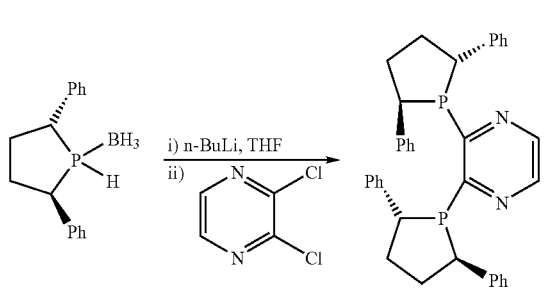

(R,R)-2,5-trans-diphenylphospholane-borane adduct (518 mg, 2.04 mmol) was dissolved in dry THF (3 ml) under nitrogen. The solution was cooled to −20° C. A solution of n-BuLi (2.5 M in hexanes, 0.82 ml, 2.04 mmol) was added dropwise and the mixture was stirred for 30 minutes (a yellow solution is formed) A solution of 2,3-dichloropyrazine (137 mg, 0.92 mmol) in THF (2 ml) was added and the solution was allowed to warm to room temperature (red/brown colour is observed instantly when the pyrazine is added). After 5 h, TMEDA (0.45 ml, 3.0 mmol, 1.5 eq.) was added and the mixture was stirred overnight. The reaction was quenched with 1M aqueous HCl (5 ml) and extracted with ethyl acetate (10 ml). The organic solution was washed with half saturated brine (10 ml), dried (MgSO$_4$), filtered and concentrated under reduced pressure. The residue was chromatographed on silica, eluting with ethyl acetate/heptane (1:8) to give the title compound as a yellow solid (105 mg, 0.19 mmol, 21%).

$^1$H NMR (400 MHz, CDCl$_3$) δ ppm 8.36 (2H, s), 7.35-7.21 (10H, m), 6.48 (2H, t, J 7 Hz), 6.40 (4H, d, J 8 Hz), 6.24 (4H, t, J 8 Hz), 4.27-4.20 (2H, m), 3.80-3.69 (2H, m), 2.54-2.43 (2H, m), 2.07-1.99 (4H, m) and 1.80-1.66 (2H, m).

$^{13}$C NMR (100 MHz, CDCl$_3$) δ ppm 163.9 (br d), 144.6 (t, J 10 Hz), 142.4, 139.9, 129.4 (t, J 5 Hz), 128.5, 127.5 (m), 126.1, 125.9, 50.0 (t, J 10 Hz), 43.8, 38.9 and 33.5.

$^{31}$P NMR (162 MHz, CDCl$_3$) δ ppm 7.2.

Example 9

Synthesis of 2,3-Bis[(R,R)-2,5-diphenyl-phospholan-1-yl]-pyrazine-(1,5-cyclooctadiene) rhodium (I) tetrafluoroborate

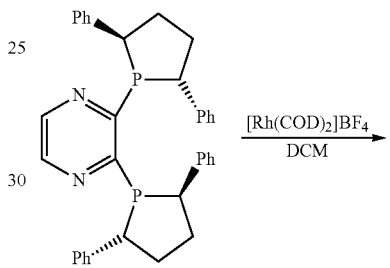

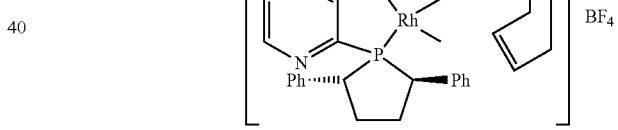

2,3-Bis[(R,R)-2,5-diphenyl-phospholan-1-yl]-pyrazine (50 mg, 0.09 mmol) and [Rh(COD)$_2$]BF$_4$ (36 mg, 0.09 mmol) were charged to a Schlenk flask. The flask was evacuated and filled with nitrogen (×5). Degassed DCM (1 ml) was added (a deep red solution forms) and the mixture was stirred for 3 h. The solvent was evaporated and the residue was washed with degassed ether (4×2 ml) and dried to give the title compound as an orange solid (76 mg, 0.088 mmol, 98%).

$^1$H NMR (400 MHz, CDCl$_3$) δ ppm 9.10 (2H, br d), 7.26-7.12 (12H, m), 6.83 (4H, d, J 8 Hz), 6.76-6.73 (4H, m), 5.67-5.60 (2H, m), 4.56-4.46 (2H, m), 4.26-4.19 (2H, m), 3.85-3.78 (2H, m), 2.97-2.84 (2H, m), 2.79-2.65 (2H, m), 2.56-2.41 (4H, m), 2.24-2.14 (2H, m), 1.89-1.78 (2H, m), 1.73-1.62 (2H, m) and 1.30-1.20 (2H, m).

$^{13}$C NMR (100 MHz, CDCl$_3$) δ ppm 158.3 (t, J 49 Hz), 147.5, 138.5, 135.2, 129.3, 129.1, 128.7, 128.1, 128.0, 127.7, 104.9 (m), 98.5 (m), 52.6 (t, J 8 Hz), 49.2 (t, J 11 Hz), 33.7, 31.8, 31.7 and 28.1.

$^{31}$P NMR (162 MHz, CDCl$_3$) δ ppm 60.2 (d, J 151 Hz).

Example 10

Synthesis of 1,1'-Bis[(R,R)-2,5-diphenyl-phospholan-1-yl]-ferrocene (i) (2S,5S)-2,5-Diphenylphospholanoyl chloride

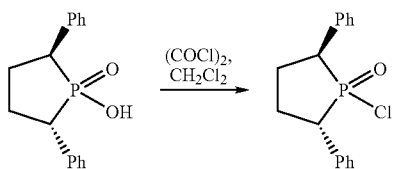

(2S,5S)-1-Hydroxy-1-oxo-2,5-trans-diphenylphospholane (5.0 g, 18.36 mmol) was placed in a flask. This was purged with nitrogen, then anhydrous dichloromethane (50 ml) was added. The suspension was cooled to 0-5° C., then oxalyl chloride (3.2 ml, 36.7 mmol) was added over 20 minutes. The suspension was stirred at 0-5° C. for 1 h, then allowed to warm to room temperature and stirred for 22 h. Anhydrous toluene (20 ml) was added to the solution, then the solvent was evaporated to give (2S,5S)-Diphenylphospholanoyl chloride as a white solid (5.38 g, quant.)

mp 133-136° C.

$^1$H NMR (400 MHz, CDCl$_3$) δ ppm 3.85-3.75 (1H, m), 3.73-3.63 (1H, m), 2.78-2.61 (1H, m), 2.59-2.42 (1H, m) and 2.37-2.19 (2H, m).

$^{13}$C NMR (100 MHz, CDCl$_3$) 135.1 (d, $J_{C—P}$=5.9 Hz), 134.2 (d, $J_{C—P}$=6.4 Hz), 129.3 (d, $J_{C—P}$=2.2 Hz), 129.2, 129.2 (d, $J_{C—P}$=3.5 Hz), 128.3 (d, $J_{C—P}$=4.6 Hz), 128.1 (d, $J_{C—P}$=4.2 Hz), 128.0 (d, $J_{C—P}$=3.9 Hz), 52.5 (d, $J_{C—P}$=53.7 Hz), 51.7 (d, $J_{C—P}$=68.1 Hz), 30.9 (d, $J_{C—P}$=14.1 Hz) and 25.7 (d, $J_{C—P}$=14.8 Hz).

$^{31}$P NMR (162 MHz, CDCl$_3$) δ ppm+80.9.

Anal. Calcd for C$_{16}$H$_{16}$ClPO (290.73): C, 66.10; H, 5.55; Cl, 12.19. Found: C, 66.21; H, 5.53; Cl, 11.93.

(ii) (2S,5S)-2,5-Diphenylphospholane-1-oxide

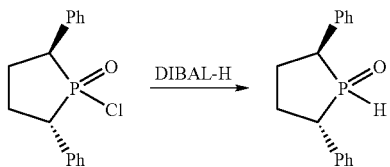

(2S,5S)-2,5-Diphenylphospholanoyl chloride (4.80 g, 16.5 mmol) was placed in a dry flask. This was purged with nitrogen, then anhydrous dichloromethane (38 ml) was added. The solution was cooled to −70° C., then DIBAL-H (1.0 M solution in dichloromethane, 17.3 ml) was added over 40 minutes. The solution was stirred at −70° C. for 1 h, then quenched with methanol (3.8 ml) over 15 minutes, after which the solution was allowed to warm to room temperature. 1 M citric acid (50 ml) was added, then the mixture was extracted with dichloromethane (2×20 ml). The combined organic layers were washed with brine (50 ml), which was back-extracted with dichloromethane (2×20 ml). The combined organic layers were dried (Na$_2$SO$_4$), filtered, and the solvent was evaporated. The solid was dissolved in dichloromethane (15 ml) and heptane (60 ml) was added while stirring. The solid was collected by filtration and dried to give (2S,5S)-diphenylphospholane-1-oxide as a white solid (3.07 g, 73%).

mp 141-143° C.

[α]$_D^{25}$-61.4, c=1.02, CHCl$_3$.

$^1$H NMR (400 MHz, CDCl$_3$) δ ppm 7.41-7.26 (110H, m), 7.18 (1H, dq, J 470, 2.8 Hz), 3.63-3.52 (1H, m), 3.32-3.25 (1H, m), 2.70-2.49 (2H, m), 2.44-2.32 (1H, m) and 2.07-1.95 (1H, m).

$^{13}$C NMR (100 MHz, CDCl$_3$) 136.8 (d, $J_{C—P}$ 2.8 Hz), 135.6 (d, $J_{C—P}$ 5.7 Hz), 129.6, 129.5, 129.2, 127.9 (d, $J_{C—P}$ 5.6 Hz), 127.7 (d, $J_{C—P}$ 2.1 Hz), 127.6 (d, $J_{C—P}$ 2.1 Hz), 48.9 (d, $J_{C—P}$ 60.0 Hz), 45.9 (d, $J_{C—P}$ 59.4 Hz), 33.4 (d, $J_{C—P}$ 7.2 Hz) and 33.4 (d, $J_{C—P}$ 10.9 Hz).

$^{31}$P NMR (162 MHz, CDCl$_3$) δ ppm+55.2.

HRMS (ESI, M+Na)$^+$: (m/z) calcd for C$_{16}$H$_{17}$PO: 279.091. Found 279.087.

(i) (2S,5S)-1-Chloro-2,5-Diphenylphospholane

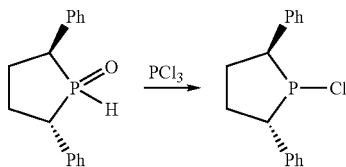

(2S,5S)-Diphenylphospholane-1-oxide (1.83 g, 1.95 mmol) was suspended in 40 mL of toluene and solution was cooled −40° C. To this suspension was added 3.92 g (28.6 mmol) of PCl$_3$ dissolved in 4 mL of toluene within 1 min. Solution was warmed to r.t. and stirred overnight resulting in formation of white sticky solid and colorless solution. Solution was transferred into another vessel and solvent was removed under reduced pressure leaving oily residue. Toluene was added (30 mL) and solvent was removed again under reduced pressure leaving 1.918 g of product as a colorless oil. Yield 97.8%.

$^1$H NMR (C$_6$D$_6$, 23° C., 300 MHz): δ 6.97-715 (10H, m), 3.75 (1H, td, $^3J_{H-H}$ 8.7 Hz, $^2J_{H-P}$ 2.1 Hz), 3.11 (1H, ddd, $^2J_{H-P}$ 33.6 Hz, $^3J_{H-H}$ 12.6 Hz, $^3J_{H-H}$ 6.0 Hz), 2.24-2.49 (2H, m), 1.97-2.08 (1H, m), 1.50-1.65 (1H, m).

$^{13}$C NMR (C$_6$D$_6$, 23° C., 75 MHz): δ 141.92 (d, $^2J_{C—P}$=19.8 Hz, quat.), 137.09 (quat.), 129.05, 128.54, 128.51 (d, $^3J_{C—P}$ 3.8 Hz), 128.01 (d, $^3J_{C—P}$ 8.4 Hz), 126.82, 126.79, 58.16 (d, $^2J_{C—P}$ 32.8 Hz), 53.64 (d, $^2J_{C—P}$ 32.8 Hz), 34.68 (d, $^3J_{C—P}$ 2.3 Hz), 31.91 (d, $^3J_{C—P}$ 2.3 Hz).

$^{31}$P NMR (C$_6$D$_6$, 23° C., 121, MHz): δ 137.687/137.656 in 2:1 ratio ($^{35}$Cl/$^{37}$Cl isotopic shift).

(iv) 1,1'-Bis[(2S,5S)-Diphenylphospholano]ferrocene

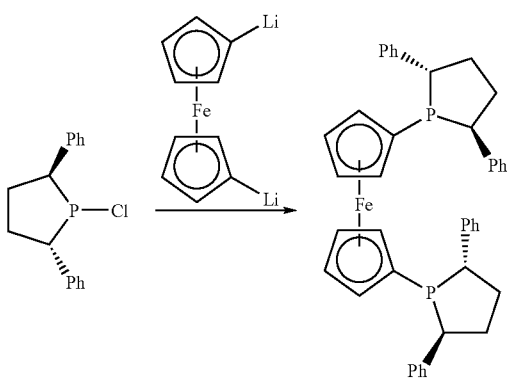

To a 40 ml chilled (−40° C.) solution of (2S,5S)-1-chloro-2,5-diphenylphospholane (0.900 g, 3.28 mmol) in toluene was added 0.5145 g (1.64 mmol) of ferrocene dilithium TMEDA complex (J. J. Bishop, A. Davison, M. L. Katcher, D. W. Lichtenberg, R. E. Merrill and J. C. Smart, *J. Organomet. Chem.* 1971, 27, 241-249) as a solid. Reaction mixture was stirred at room temperature for 24 hr. Methylene chloride (10 ml) was added to the mixture to dissolve some of the product that crystallized. The $^{31}P\{^1H\}$ of this reaction mixture showed formation of the desired product in about 90% together with about 10% of mono-phosphine, (2S,5S)-diphenylphospholano]ferrocene). Solvent was removed under reduced pressure to give yellow-orange solid. Toluene was added (12 ml) and suspension was stirred for 1 hr. Yellow solid was collected on the frit, washed with 10 ml of hexane and dried under reduced pressure to give 0.76 g of clean product 8. Yield 70%.

$^1H$ NMR ($C_6D_6$, 23° C., 300 MHz): δ 7.47 (4H, dm, $^3J_{H-H}$ 8.4 Hz, ortho$^1$-H), 7.24 (4H, tm, $^3J_{H-H}$ 7.8 Hz, meta$^1$-H), 7.10 (2H, tm, $^3J_{H-H}$ 7.7 Hz, para$^1$-H), 6.92-6.99 (4H, m), 6.84-6.92 (6H, m), 4.08 (2H, m, Cp), 4.06 (2H, m, Cp), 3.75 (2H, m, Cp), 3.72 (2H, m, CH), 3.47 (2H, m, Cp), 3.30 (2H, m, CH), 2.47 (2H, m, $CH_2$), 1.95-2.18 (4H, m, $CH_2$), 1.64 (2H m, $CH_2$).

$^{13}C$ NMR ($C_6D_6$, 23° C., 75 MHz): δ 146.24 (d, $^2J_{C-P}$=18.9 Hz, quat.), 139.16 (quat.), 128.95 (meta-C), 128.46 (d, $^3J_{C-P}$ 10.4 Hz, ortho-C), 128.09 (d, $^3J_{C-P}$ 3.6 Hz, ortho-C), 127.96, 126.27 (para-C), 125.69 (para-C), 77.33 (d, $J_{C-P}$ 31.1 Hz, Cp), 76.02 (d, $^1J_{C-P}$ 27.5 Hz, Cp, quat.), 72.67 (d, $J_{C-P}$ 7.9 Hz, Cp). 71.63 (s, Cp), 69.86 (d, $J_{C-P}$ 4.2 Hz, Cp), 50.07 (d, $^2J_{C-P}$ 15.9 Hz, CH), 48.85 (d, $^2J_{C-P}$ 14.6 Hz, CH), 39.20 (s, $CH_2$), 33.73 (d, $^3J_{C-P}$ 3.6 Hz, $CH_2$).

$^{31}P$ NMR ($C_6D_6$, 23° C., 121 MHz): δ 12.19.

HSQC ($C_6D_6$, 23° C.): δ 128.95/7.24, 128.46/7.47, 128.09/(6.92-6.99), 127.96/(6.84-6.92), 126.27/7.10, 125.69/(6.92-6.99), 77.33/3.47, 72.67/3.75, 71.63/4.08, 69.86/4.06, 50.07/3.30, 48.85/3.72, 39.20/(2.47, 1.64), 33.73/(1.95-2.18).

HRMS (ESI, M+H)$^+$:(m/z) calcd for $C_{42}H_{41}FeP_2$: 663.203. Found 663.200. Anal. Calcd for $C_{42}H_{40}FeP_2$ (662.58): C, 76.14; H, 6.09. Found: C, 76.02; H, 5.88.

Example 11

Synthesis of 1,1'-Bis[(2S,5S)-Diphenylphospholano]ferrocene(1,5-cyclooctadiene)rhodium(I) tetrafluoroborate 1,1'-Bis[(2S,5S)-2,5-diphenylphospholano]ferrocene 8 (0.354 g, 0.53 mmol) and $Rh(COD)_2BF_4$ (0.2171 g, 0.53) were dissolved in 10 ml of $CH_2Cl_2$ giving rise to red-orange solution. After stirring for 30 min. the $^{31}P\{^1H\}$ NMR showed clean formation of the desired complex. Solvent was reduced to about 1 ml and 0.5 ml of ether was added causing formation of orange-red crystals. After 30 min. more ether was added (1 ml) and solution was left standing for 2 hr. Solvent was decanted and the remaining crystals were washed with ether (2 ml) and then dried under reduced pressure to give 0.446 g of product as red-orange crystals. Crystals contain one molecule of methylene chloride Yield 79.8%.

$^1H$ NMR ($CD_2Cl_2$, 23° C., 300 MHz): δ ppm 7.81 (4H, m, ortho$^1$-H), 7.40 (6H, m, meta$^1$/para$^1$), 7.13 (6H, m, meta$^2$/para$^2$), 6.68 (4H, d, $^3J_{H-H}$ 7.5 Hz, ortho$^2$-H), 5.59 (2H, br. t., $^3J_{H-H}$ 6.9 Hz, COD), 4.50 (2H, br. COD), 4.42 (6H, m, Cp), 4.14 (2H, qm, $J_{H-P}$ 9.6 Hz, PCH), 3.60 (2H, m, Cp), 3.36 (2H, dd, $J_{H-P}$ 11.7 Hz, $^3J_{H-H}$ 6.3 Hz, PCH), 2.61-2.80 (2H, m, $PCHCH_2$), 2.24-2.46 (4H, m, $PCHCH_2$), 1.70-2.50 (10H, m, $PCHCH_2$/COD).

$^{13}C$ NMR ($CD_2Cl_2$, 23° C., 75 MHz): δ ppm 140.21 (t, $J_{C-P}$ 2.4 Hz, quat.), 136.29 (quat.), 129.17 (meta$^1$), 128.89 (t, $J_{C-P}$ 1.8 Hz, ortho$^2$), 128.76 (t, $J_{C-P}$ 3.7 Hz, ortho$^1$), 128.38 (meta$^2$), 128.13 (para$^1$), 127.28 (para$^2$), 98.41 (dt, $J_{C-Rh}$=9.3 Hz, $J_{C-P}$=2.4 Hz, COD), 89.57 (q, J 7.2 Hz, COD), 76.54 (dt, J 18.3 Hz, J=7.9 Hz, Cp), 75.38 (t, $J_{C-P}$ 4.3 Hz, Cp), 73.11 (Cp), 72.65 (t, $J_{C-P}$ 1.8 Hz, Cp), 70.92 (d, $^1J_{C-P}$ 42.7 Hz, Cp, quat.), 49.72 (dt, J 20.7 Hz, J 8.5 Hz, PCH), 46.47 (dt, J 14.6 Hz, J 10.3 Hz, PCH), 35.35 ($PCHCH_2$), 33.23 ($PCHCH_2$), 33.13 (COD), 28.12 (COD).

HSQC ($CD_2Cl_2$, 23° C.): δ ppm 129.17/7.40, 128.89/6.68, 128.76/7.81, 128.38/7.13, 128.13/7.40, 127.28/7.13, 98.41/5.59, 89.57/4.50, 76.54/3.60, 75.38/4.42, 73.11/4.42, 72.65/4.42, 49.72/4.14, 46.47/3.30, 35.35/(2.70, 2.31), 33.23/(2.38, 2.18), 33.13/1.99, 28.12/1.85.

$^{31}P$ NMR ($CD_2Cl_2$, 23° C., 121 MHz): δ ppm 36.79 (d, $^1J_{P-Rh}$=146.5 Hz).

$^{19}F$ NMR ($CD_2Cl_2$, 23° C., 282 MHz): δ ppm −153.43.

HRMS (ESI, M$^+$): (m/z) calcd for $C_{50}H_{52}FeP_2Rh$: 873.195. Found 873.194.

Anal. Calcd for $C_{51}H_{54}FeCl_2P_2RhBF_4$: C, 58.60; H, 5.21. Found: C, 58.76; H, 5.17.

Example 12

Asymmetric Hydrogenation Processes Using Transition Metal Catalyst Complexes of Examples 5, 7, 9 & 11

(i) General Procedures for Rhodium Catalysed Hydrogenations (Representative Procedures Employing the Complex of Example 5

Hydrogenation of Dimethyl Itaconate

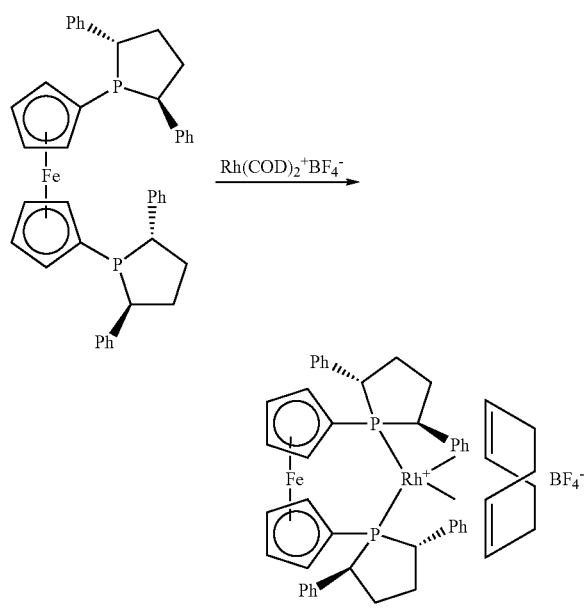

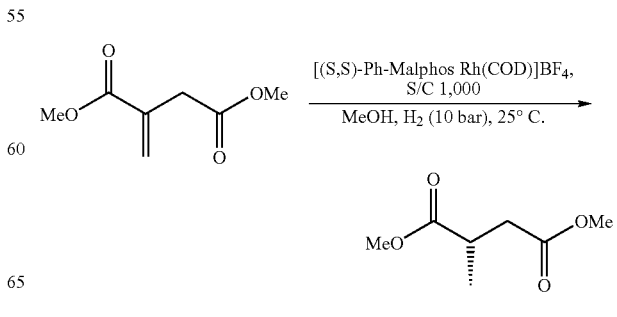

The reaction was carried out in an Argonaut Endeavor hydrogenation vessel. The glass liner was charged with dimethyl itaconate (316 mg, 2.0 mmol) and 3,4-bis[(S,S)-2,5-diphenyl-phospholan-1-yl]-furan-2,5-dione-(1,5-cyclooctadiene) rhodium(I) tetrafluoroborate (1.7 mg, 0.002 mmol, S/C 1000). The vessel was charged to 10 bar nitrogen and vented (×5). Degassed methanol (4 ml) was added. The vessel was charged to 10 bar nitrogen and vented (×2). Stirring was commenced at 1000 rpm and the contents were heated to 25° C. The vessel was charged to 10 bar hydrogen. Hydrogen uptake was complete after 16 h. The mixture was vented and evaporated to give (S)-2-methylsuccinic acid dimethyl ester, conversion 100%, ee 96.6% (Chiraldex GTA, 30 m×0.25 mm, injector/detector 180° C., helium 14 psi, 90° C. for 6 min then ramp at 1° C./min to 105° C., retention times S 10.11 minutes, R 10.48 minutes). In comparison, much lower enantioselectivity, of 60.2% ee, is reported by Holz, J. et al, ibid., for the same transformation, at S/C 100 in methanol, catalysed by the corresponding rhodium complex of Me-Malphos [i.e. the analogue of ligand (7) with Me groups at the 2- and 5-position of each phospholane ring]. Holz, J. et al also report that a change of solvent, to THF, increases the enantioselectivity to 86% ee but this still falls short of the 96.6% ee achieved in the current example at a higher S/C ratio.

Hydrogenation of methyl 2-acetamidoacrylate

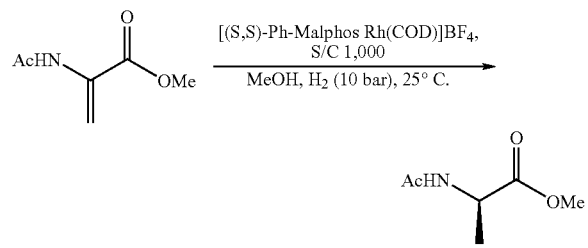

(R)-2-Acetylaminopropionic acid methyl ester, conversion 100%, ee 99.7% (Chirasil Dex CB, 25 m×0.25 mm, injector/detector 200° C., helium 20 psi, 130° C. for 10 minutes then ramp at 15° C./min to 200° C., retention times S 2.91 minutes, R 2.98 minutes).

Hydrogenation of Methyl Acetamidocinnamate

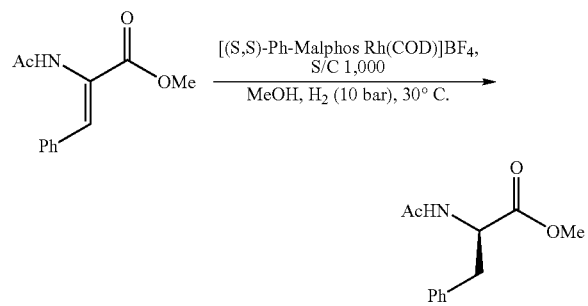

(R)-2-Acetylamino-3-phenyl-propionic acid methyl ester, conversion 100%, ee 98.8% (Chirasil Dex CB, 25 m×0.25 mm, injector/detector 200° C., helium 20 psi, 150° C. for 21 minutes then ramp at 15° C./min to 200° C., hold for 5 minutes, retention times R 17.65 minutes, S 17.92 minutes).

2-Acetamidoacrylic acid and acetamidocinnamic acid were hydrogenated using the same general procedure, derivatised using TMS-diazomethane and analysed using the same method described for the corresponding methyl esters.

Similar procedures were applied in the screening of transition metal catalyst complexes of examples 7, 9 & 11. The following are specific procedures demonstrating the catalytic utility of the transition metal complex of example 11.

Hydrogenation of Methyl 2-acetamido-3,3-diphenylacrylate

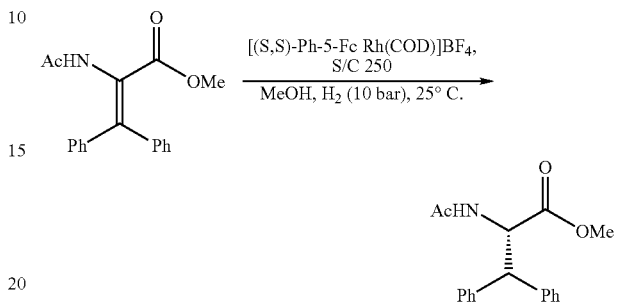

(R)-2-Acetylamino-3,3-diphenylpropionic acid methyl ester, reaction time 6 h, conversion 100%. $[\alpha]_D^{25}$-101.6 (c=1.02, CHCl$_3$). ee 80.7% (SFC, 2× Chiralpak AD-H columns, 10% methanol, 3000 psi CO$_2$, 35° C., flow rate 3 ml/minute, retention times R 5.2 minutes, S 10.1 minutes). Comparative examples have been disclosed by Boulton (Boulton, L. T., WO 2006127273).

Hydrogenation of (E)-2-Methylcinnamic Acid tert-butylamine salt

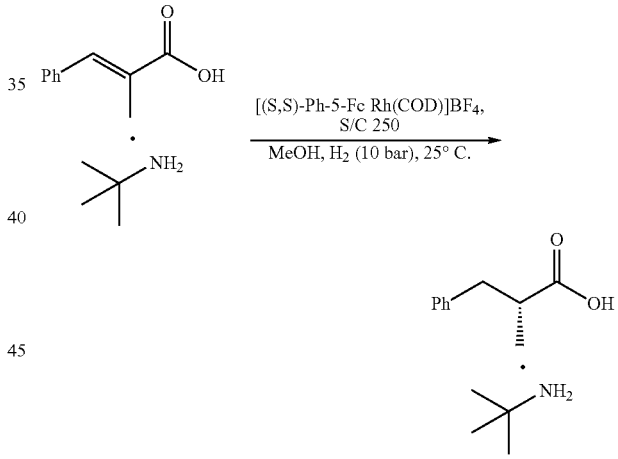

(R)-2-Methyl-3-phenylpropionic acid tert-butylamine salt, reaction time 40 minutes, conversion 100%. The free acid was liberated by partitioning between dichloromethane and 2M HCl. The organic layer was dried (Na$_2$SO$_4$), filtered and the solvent was evaporated, then the product was distilled (kugelrohr, 150° C., 0.5 mbar) to give (R)-2-Methyl-3-phenylpropionic acid as a colorless liquid. $[\alpha]_D^{25}$-22.7, c=1.02, CHCl$_3$. Lit. (E. Tyrell, M. W. H. Tang, G. A. Skinner and J. Fawcett, *Tetrahedron*, 1996, 52, 9841-9852, $[\alpha]_D^{20}$-23.1 c=1, CHCl$_3$). ee 85% (derivatised using TMS-diazomethane, Chirasil Dex CB column, 25 m×0.25 mm, injector/detector 200° C., helium 20 psi, 100° C. for 21 minutes then ramp at 15° C./min to 200° C., hold for 5 minutes, retention times R 30.40 minutes, S 31.06 minutes, (E)-methyl 2-methylcinnamate, 34.79 minutes). $^1$H NMR analysis of the (S)-methyl mandelate (E. Tyrell, M. W. H. Tang, G. A. Skinner and J. Fawcett, *Tetrahedron*, 1996, 52, 9841-9852) confirmed assignment of (R)-configuration.

Hydrogenation of (E)-2-phenylcinnamic acid tert-butylamine salt

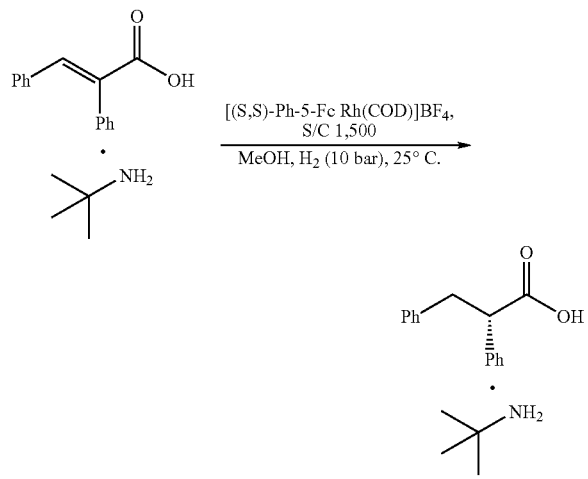

(S)-2-Methyl-3-phenylpropionic acid tert-butylamine salt, reaction time 40 minutes, conversion 100%, ee 96.5% (SFC, 2× Chiralpak AD-H columns, 10% methanol, 3000 psi $CO_2$, 35° C., flow rate 3 ml/minute, retention times R 7.1 minutes, S 7.7 minutes, (E)-phenylcinnamic acid 12 minutes). The free acid was liberated by partitioning between dichloromethane and 2M HCl. The organic layer was dried ($Na_2SO_4$), filtered and the solvent was evaporated to give (R)-2-Methyl-3-phenylpropionic acid as a pale yellow solid. $[\alpha]_D^{20}$+98.6, c=2.03, $CHCl_3$. $[\alpha]_D^{20}$+100.6, c=0.54, acetone. $[\alpha]_D^{20}$+103.5 (c=1.00, MeOH). Lit. (M. B. Watson and G. W. Youngson, *J. Chem. Soc. C,* 1968, 258-261; +140.8, c=2.04, $CHCl_3$). $^1$H NMR analysis of the (S)-methyl mandelate (E. Tyrell, M. W. H. Tang, G. A. Skinner and J. Fawcett, *Tetrahedron,* 1996, 52, 9841-9852) confirmed assignment of (S)-configuration.

Hydrogenation of (E)-2-Isopropyl-3-(2-(3-methoxy (propyloxy)-4-methoxyphenyl)acrylic acid tert-butylamine salt (For Preparation, see P. Herold, P and S. Stutz, S, WO 2002002500)

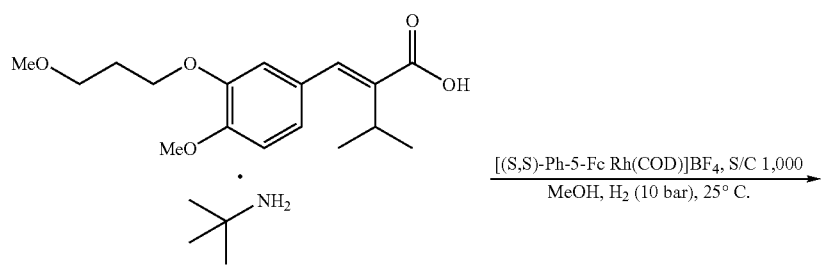

(S)-2-Isopropyl-3-(2-(3-methoxy(propyloxy)-4-methoxyphenyl)propionic acid tert-butylamine salt, reaction time 1 h, conversion 100%, ee 84.6% (SFC, 2× Chiralpak AD-H columns, 10% methanol, 3000 psi $CO_2$, 35° C., flow rate 3 ml/minute, retention times S 4.6 minutes, R 5.0 minutes). The free acid was liberated by partitioning between dichloromethane and 2M HCl. The organic layer was dried ($Na_2SO_4$), filtered and the solvent was evaporated to (S)-2-Isopropyl-3-(2-(3-methoxy(propyloxy)-4-methoxyphenyl) propionic acid as a pale yellow oil. $[\alpha]_D^{20}$–33.0, c=1.01, $CH_2Cl_2$. Lit. (enantiomer, R. Goeschke, S. Stutz, W. Heizelmann and J. Maibaum, *Helv. Chim. Acta,* 2003, 86, 2848-2870); $[\alpha]_D^{20}$+42.5, c=1.0, $CH_2Cl_2$. Comparison with a sample made using (R)-WalPhos (T. Sturm, W. Weissensteiner and F. Spindler, *Adv. Synth. Catal.,* 2003, 455, 160-164) using the assay above confirmed assignment of (R)-configuration.

(ii) Summary of Asymmetric Hydrogenation Screening with the Transition Metal Catalyst Complex of Example 7

| Substrate | S/C | Conditions | Conv. (%) | ee (%) |
|---|---|---|---|---|
| 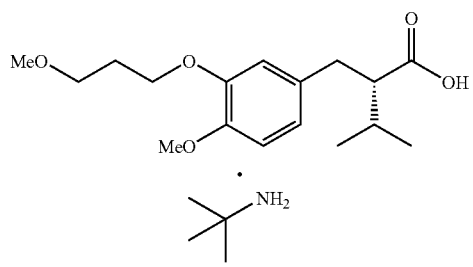 | 1000 | MeOH, 25° C., 10 bar $H_2$, 15 mins | 100 | 99.8 (S) |
| | 1000 | MeOH, 25° C., 10 bars $H_2$, 10 mins | 100 | 99.9 (R) |

-continued

| Substrate | S/C | Conditions | Conv. (%) | ee (%) |
|---|---|---|---|---|
| 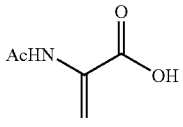 | 1000 | MeOH, 25° C., 10 bar H$_2$, 10 mins | 100 | 98.7 (R) |
| 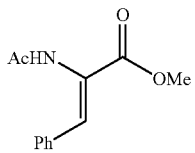 | 1000 | MeOH, 30° C., 10 bar H$_2$, 20 mins | 100 | >99.5 (R) |
| 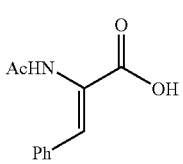 | 1000 | MeOH, 30° C., 10 bar H$_2$, 25 mins | 100 | 99.5 (R) |

(iii) Summary of Asymmetric Hydrogenation Screening with the Transition Metal Catalyst Complex of Example 9

| Substrate | S/C | Conditions | Conv. (%) | ee (%) |
|---|---|---|---|---|
| 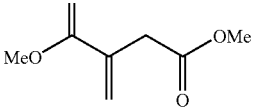 | 1000 | MeOH, 25° C., 10 bar H$_2$, 18 h | 98 | 78 (R) |
| 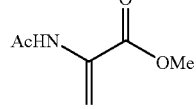 | 1000 | MeOH, 25° C., 10 bar H$_2$, 18 h | 94 | 94 (R) |

(iv) Summary of Asymmetric Hydrogenation Screening with the Transition Metal Catalyst Complex of Example 11

| Substrate | S/C | Conditions | Conv. (%) | ee (%) |
|---|---|---|---|---|
| 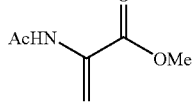 | 1000 | MeOH, 25° C., 10 bar H$_2$, 100 mins | 100 | 29 (R) |
| 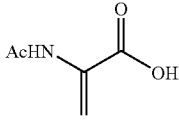 | 1000 | MeOH, 25° C., 10 bar H$_2$, 80 mins | 100 | 49 (R) |
| 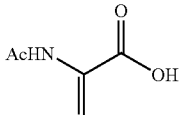 | 1000 | MeOH, 30° C., 10 bar H$_2$, 15 mins | 100 | 56 (R) |
| 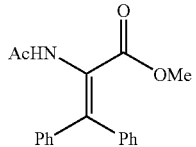 | 250 | MeOH, 30° C., 10 bar H$_2$, 40 mins | 100 | 80.7 |
| 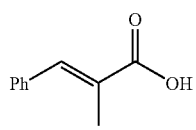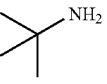 | 1000 | MeOH, 30° C., 10 bar H$_2$, 40 mins | 100 | 85 (R) |

-continued

| Substrate | S/C | Conditions | Conv. (%) | ee (%) |
|---|---|---|---|---|
| Ph-CH=C(Ph)-COOH · tBu-NH2 | 1500 | MeOH, 25° C., 10 bar H2, 40 mins | 100 | 96.5 (S) |
| MeO(CH2)3O-C6H3(OMe)-CH=C(iPr)-COOH · tBu-NH2 | 1000 | MeOH, 25° C., 10 bar H2, 1 h | 100 | 84.6 (S) |

(v) Comparative Examples for the Transition Metal Catalyst Complex of Example 11 with Substrate Below Using [L Rh(COD)]+ Complexes of Different Ligands Ph-CH=C(Me)-COOH · tBu-NH2

| Ligand | S/C | Conditions | Conv. (%) | ee (%) |
|---|---|---|---|---|
| (R,R)-Me-5-Fc | 1000 | MeOH, 25° C., 10 bar H2, 18 h. | 100 | 52 (R) |
| (R,R)-Et-5-Fc | 1000 | MeOH, 25° C., 10 bar H2, 18 h. | 100 | 45 (R) |
| (R,R)-iPr-5-Fc | 1000 | MeOH, 25° C., 10 bar H2, 18 h. | 100 | 69 (S) |
| (R,R)-Ph-BPE | 1000 | MeOH, 25° C., 10 bar H2, 18 h. | 65 | 25 (S) |
| (S,S)-ligand of example 6 (complex of example 7) | 1000 | MeOH, 25° C., 10 bar H2, 18 h. | 10 | 0 |

(vi) Comparative Examples for the Transition Metal Catalyst Complex of Example 11 with Substrate Below Using [L Rh(COD)]+ Complexes of Different Ligands Ph-CH=C(Ph)-COOH · tBu-NH2

| Ligand | S/C | Conditions | Conv. (%) | ee (%) |
|---|---|---|---|---|
| (R,R)-Me-5-Fc | 1000 | MeOH, 25° C., 10 bar H2, 18 h. | 100 | 46 (S) |
| (R,R)-Et-5-Fc | 1000 | MeOH, 25° C., 10 bar H2, 18 h. | 100 | 65 (S) |
| (R,R)-Pr-5-Fc | 1000 | MeOH, 25° C., 10 bar H2, 18 h. | 65 | 65 (R) |
| (R,R)-Ph-BPE | 1000 | MeOH, 25° C., 10 bar H2, 18 h. | 50 | 20 (R) |
| (S,S)-ligand of example 6 (complex of example 7) | 1000 | MeOH, 25° C., 10 bar H2, 18 h. | 5 | 11 (R) |

(vii) Comparative Examples for the Transition Metal Catalyst Complex of Example 11 with Substrate Below Using [L Rh(COD)]⁺ Complexes of Different Ligands

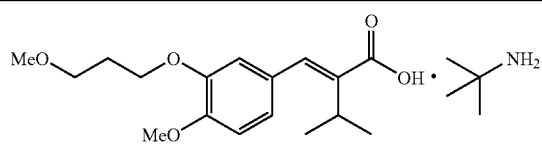

| Ligand | S/C | Conditions | Conv. (%) | ee (%) |
|---|---|---|---|---|
| (S,S)-Me-DuPhos | 250 | MeOH, 25° C., 10 bar H₂, 16 h. | 34 | 0 |
| (S,S)-Me-5-Fc | 250 | MeOH, 25° C., 10 bar H₂, 16 h. | 100 | 61 |
| (S,S)-Et-5-Fc | 250 | MeOH, 25° C., 10 bar H₂, 16 h. | 100 | 57 |
| (S,S)-iPr-5-Fc | 250 | MeOH, 25° C., 10 bar H₂, 16 h. | 100 | 69 |
| (R,R)-Ph-BPE | 250 | MeOH, 25° C., 10 bar H₂, 16 h. | 100 | 25 |

Example 13

Asymmetric Hydroformylation Processes

Hydroformylation solutions were prepared by addition of ligand and Rh(CO)₂(acac) stock solutions to toluene solvent followed by addition of olefin solution. Total amount of liquids in each reactor cell was 4.5 ml. Ligand solutions (0.03 M for bidentate ligands and Rh(CO)₂(acac) (0.05 M) were prepared in the dry box by dissolving appropriate amount of compound in toluene at room temperature. The allyl cyanide solution was prepared by mixing 15.3206 g of allyl cyanide, 3.2494 g of dodecane (as a GC internal standard) and 6.3124 g of toluene (1:0.1:0.3 molar ratio). The styrene solution was prepared by mixing 14.221 g of styrene and 6.978 g of dodecane (1:0.3 molar ratio). The vinyl acetate solution was prepared by mixing 13.426 g of vinyl acetate and 7.969 g of dodecane (1:0.3 molar ratio). The styrene:allyl cyanide:vinyl acetate:dodecane solution was prepared by mixing 11.712 g of styrene, 7.544 g of allyl cyanide, 9.681 g of vinyl acetate and 5.747 g of dodecane (1:1:1:0.3 molar ratio).

Hydroformylation reactions were conducted in an Argonaut Endeavor® reactor system housed in an inert atmosphere glove box. The reactor system consists of eight parallel, mechanically stirred pressure reactors with individual temperature and pressure controls. Upon charging the catalyst solutions, the reactors were pressurized with 150 psi of syn gas (H₂:CO 1:1) and then heated to the desired temperature while stirring at 800 rpm. The runs were stopped after 3 hrs by venting the system and purging with nitrogen.

The substrate to catalyst ratio was 3,000:1. 56 µL of 0.05 M Rh(CO)₂(acac) stock solutions was mixed with 187 µL of 0.03 M ligand stock solution followed by addition of 1 ml of olefin mixture solution. Solution was pressurized at 150 psi with syngas and heated at 80° C. for 3 hr. Syn gas pressure was maintained at 150 psi (gas on demand) throughout the reaction.

After 3 hrs reactors were cooled and vented. Upon opening the reactor sample from each reactor was taken out and diluted with 1.6 ml of toluene, and this solution was analyzed by gas chromatography. For analysis of styrene and vinyl acetate products Supelco's Beta Dex 225 column was used. Temperature program of 100° C. for 5 min, then 4° C./min to 160° C.; retention times: 2.40 min for vinyl acetate, 6.76 (R) and 8.56 (S) min for the enantiomers of the acetic acid 1-methyl-2-oxo-ethyl ester (branched regioisomer), 11.50 min for acetic acid 3-oxo-propyl ester (linear regioisomer), 12.11 (R) and 12.34 (S) min for the enantiomers of 2-phenyl-propionaldehyde (branched regioisomer) and 16.08 min for 3-phenyl-propionaldehyde (linear regioisomer).

For allyl cyanide product analysis Astec Chiraldex A-TA column was used. Temperature program of 90° C. for 7 min, then 5° C./min to 180° C.; retention times: 5.55 min for allyl cyanide, 14.79 (S) and 15.28 (R) min for the enantiomers of the 3-methyl-4-oxo-butyronitrile (branched regioisomer), and 19.46 for the 5-oxo-pentanenitrile (linear regioisomer).

The following table shows Percent conversion (Conv.), branched:linear ratio (b:1), and enantioselectivity (% e.e.) for hydroformylation of styrene, allyl cyanide, and vinyl acetate with chiral phosphorus ligands. Note that Ligand 7 shows remarkably improved results as compared to the similar compound having methyl substituents rather than phenyl substituents.

| Ligand | Styrene | | | Allyl cyanide | | | Vinyl acetate | | |
|---|---|---|---|---|---|---|---|---|---|
| | Conv | b:l | % e.e. | Conv | b:l | % e.e. | Conv. | b:l | % e.e. |
| 7 | 43 | 38.5 | 90(S) | 76 | 8.1 | 81(S) | 48 | 111 | 68(S) |
| 9 | 98 | 36.4 | 90(S) | 100 | 6.0 | 77(R) | 96 | 190 | 70(S) |
| 8 | 95 | 39.7 | 90(R) | 100 | 7.1 | 79(R) | 92 | 221 | 69(S) |
| 6* | 12 | 20 | 1(S) | 44 | 4.5 | 2(S) | 24 | 603 | 24(R) |
| Comparative example similar to (7) but with methyl groups in the place of the phenyl groups | 9 | 14 | 49(S) | 31 | 6.1 | 38(S) | 16 | 75 | 30(R) |

*0.5 ml of olefin mixture solution was used and L:Rh was 1.2

The invention claimed is:

1. An enantiomerically enriched compound of formula (1) or the opposite enantiomer thereof

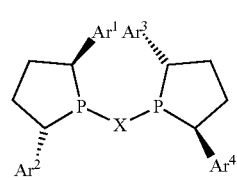

(1)

wherein the bridging group X is the formula (5) in which * denotes points of

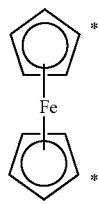
(5)

attachment to phosphorus atoms and each of Ar¹—Ar⁴ is phenyl.

2. The compound of claim 1 of formula (10), wherein Ph is phenyl, or

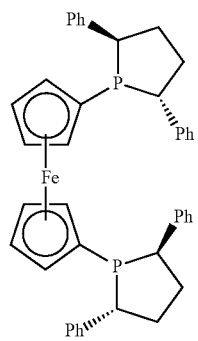
(10)

the opposite enantiomer thereof.

3. The compound of formula (10) according to claim 2, as the (R,R)-enantiomer or as the (S,S)-enantiomer.

4. A method for the manufacture of a compound according to claim 3, which comprises the following steps for the (S,S)-enantiomer or equivalent steps for the (R,R)-enantiomeric series:
(a) conversion of (S,S)-1-oxo-2,5-diphenylphospholane to an intermediate (S,S)-1-halogeno-2,5-diphenylphospholane, wherein halogeno (Z) is chloro or bromo; and
(b) coupling of (S,S)-1-halogeno-2,5-diphenylphospholane with a 1,1-dilithioferrocene

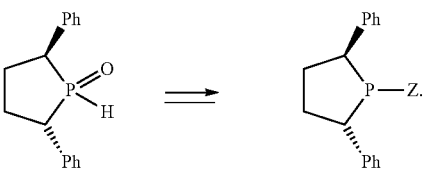

5. The method of claim 4, wherein the coupling is performed using a N,N,N,N-tetramethylethylenediamine (TMEDA) complex of 1,1'-dilithioferrocene.

* * * * *